US011020513B2

(12) United States Patent
Arps et al.

(10) Patent No.: US 11,020,513 B2
(45) Date of Patent: *Jun. 1, 2021

(54) INSERTABLE MEDICAL DEVICES HAVING MICROPARTICULATE-ASSOCIATED ELASTIC SUBSTRATES AND METHODS FOR DRUG DELIVERY

(71) Applicant: Surmodics, Inc., Eden Prairie, MN (US)

(72) Inventors: James Howard Arps, Chanhassen, MN (US); Andrew G. Bach, Edina, MN (US)

(73) Assignee: Surmodics, Inc., Eden Prairie, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/866,930

(22) Filed: Jan. 10, 2018

(65) Prior Publication Data

US 2018/0126128 A1    May 10, 2018

Related U.S. Application Data

(60) Continuation of application No. 15/227,458, filed on Aug. 3, 2016, now Pat. No. 9,895,516, which is a division of application No. 14/613,777, filed on Feb. 4, 2015, now Pat. No. 9,669,192, which is a continuation of application No. 12/383,751, filed on Mar. 27, 2009, now Pat. No. 8,951,545.

(60) Provisional application No. 61/072,234, filed on Mar. 28, 2008.

(51) Int. Cl.
| | |
|---|---|
| *A61L 29/16* | (2006.01) |
| *A61L 29/08* | (2006.01) |
| *A61M 25/10* | (2013.01) |
| *A61L 29/04* | (2006.01) |
| *A61L 29/14* | (2006.01) |
| *A61K 31/337* | (2006.01) |

(52) U.S. Cl.
CPC .......... *A61L 29/041* (2013.01); *A61K 31/337* (2013.01); *A61L 29/085* (2013.01); *A61L 29/145* (2013.01); *A61L 29/148* (2013.01); *A61L 29/16* (2013.01); *A61M 25/104* (2013.01); *A61L 2300/416* (2013.01); *A61L 2300/604* (2013.01); *A61L 2300/606* (2013.01); *A61L 2300/622* (2013.01); *A61M 25/1002* (2013.01); *A61M 2025/1004* (2013.01); *A61M 2025/105* (2013.01); *A61M 2025/1031* (2013.01); *A61M 2025/1075* (2013.01)

(58) Field of Classification Search
None
See application file for complete search history.

(56) References Cited

U.S. PATENT DOCUMENTS

| | | | |
|---|---|---|---|
| 5,102,402 A | 4/1992 | Dror et al. | |
| 5,304,121 A | 4/1994 | Sahatjian | |
| 5,414,075 A | 5/1995 | Swan et al. | |
| 5,674,192 A | 10/1997 | Sahatjian et al. | |
| 5,893,840 A | 4/1999 | Hull et al. | |
| 5,954,706 A | 9/1999 | Sahatjian | |
| 6,007,833 A | 12/1999 | Chudzik et al. | |
| 6,129,705 A | 10/2000 | Grantz | |
| 6,143,037 A | 11/2000 | Goldstein et al. | |
| 6,156,345 A | 12/2000 | Chudzik et al. | |
| 6,303,148 B1 | 10/2001 | Hennink et al. | |
| 6,364,893 B1 | 4/2002 | Sahatjian et al. | |
| 6,394,995 B1 | 5/2002 | Solar et al. | |
| 6,638,246 B1 | 10/2003 | Naimark et al. | |
| 7,060,051 B2 | 6/2006 | Palasis | |
| 7,628,344 B2 | 12/2009 | Mahakul et al. | |
| 7,794,751 B2 | 9/2010 | Chudzik et al. | |
| 2002/0082552 A1 | 6/2002 | Ding et al. | |
| 2003/0064965 A1 | 4/2003 | Richter | |
| 2003/0129130 A1 | 7/2003 | Guire et al. | |
| 2003/0203958 A1 | 10/2003 | Kunz et al. | |
| 2005/0220843 A1 | 10/2005 | DeWitt et al. | |
| 2005/0244459 A1 | 11/2005 | DeWitt et al. | |
| 2005/0255142 A1 | 11/2005 | Chudzik et al. | |
| 2006/0018277 A1 | 1/2006 | Petrovic et al. | |
| 2006/0018948 A1 | 1/2006 | Guire et al. | |
| 2007/0260054 A1 | 11/2007 | Chudzik | |
| 2009/0028956 A1 | 1/2009 | Slager et al. | |
| 2009/0124535 A1 | 5/2009 | Markland et al. | |
| 2010/0040766 A1 | 2/2010 | Chappa et al. | |
| 2010/0179475 A1* | 7/2010 | Hoffmann | A61L 29/16 604/103.02 |

FOREIGN PATENT DOCUMENTS

| | | |
|---|---|---|
| EP | 1 834 636 A1 | 9/2007 |
| JP | 9-500561 | 1/1997 |
| JP | 2001514936 A | 9/2001 |
| JP | 2002506813 A | 3/2002 |

(Continued)

OTHER PUBLICATIONS

Japanese Patent Office, App. No. 2014-209337; Office Action (Notification of Reasons for Refusal), dated Oct. 13, 2015.

(Continued)

*Primary Examiner* — H. Sarah Park

(74) *Attorney, Agent, or Firm* — Kagan Binder, PLLC

(57) ABSTRACT

The present invention provides insertable medical devices having elastic surfaces associated with bioactive agent-containing microparticulates and a coating material. Upon expansion of the elastic surfaces the microparticulates can be released to a subject.

13 Claims, 11 Drawing Sheets

(56) References Cited

FOREIGN PATENT DOCUMENTS

| JP | 2007-537005 A | 5/2008 |
|---|---|---|
| WO | 99/08729 A1 | 2/1999 |
| WO | 2007/084418 A2 | 7/2007 |

OTHER PUBLICATIONS

PCT Search Report for International Application No. PCT/US2009/001901 dated Jul. 19, 2010.
Japanese Office Action mailed in Application No. 2014-209337, dated Sep. 29, 2015, 8 pages (5 pages of English Translation and 3 pages of Official Copy).
Office Action dated Sep. 3, 2019 in Japanese Patent Application No. 2016-139332, 7 pages (4 pages of English Translation and 3 pages of Official Copy).
Office Action dated Oct. 1, 2019 in Japanese Patent Application No. 2018-108900, 5 pages (3 pages of English Translation and 2 pages of Official Copy).

\* cited by examiner

INSERTABLE MEDICAL DEVICES HAVING MICROPARTICULATE-ASSOCIATED ELASTIC SUBSTRATES AND METHODS FOR DRUG DELIVERY

CROSS-REFERENCE TO RELATED APPLICATIONS

This application is a continuation of U.S. application Ser. No. 15/227,458, filed Aug. 3, 2016, which is a divisional of U.S. application Ser. No. 14/613,777, filed Feb. 4, 2015, now issued as U.S. Pat. No. 9,669,192 on Jun. 6, 2017, which is a continuation of U.S. application Ser. No. 12/383,751, filed Mar. 27, 2006, now issued as U.S. Pat. No. 8,951,545 on Feb. 10, 2015, which claims the benefit of U.S. Provisional Application No. 61/072,234, filed on Mar. 28, 2008, and entitled INSERTABLE MEDICAL DEVICES HAVING MICROPARTICLE-ASSOCIATED ELASTIC SUBSTRATES AND METHODS FOR DRUG DELIVERY, all of which are incorporated by reference in their entirety for all purposes in this application.

FIELD OF THE INVENTION

The present invention relates to the field of drug delivery from insertable medical articles.

BACKGROUND OF THE INVENTION

The release of drugs from an implanted medical device has been shown to be beneficial for the function of devices and the treatment of various medical conditions. For example, delivery of a drug from the device surface can prevent cellular responses initiated by the presence of the implantable device. Also, drug released from the device can prevent conditions that would otherwise shorten the functional life of the device following implantation. Drug released from the device may also be directed at treating a diseased area of the body.

Some implantable devices simply have a drug applied to the device surface. Such preparations are generally undesirable because the drug can be easily removed from the surface during insertion. In addition, release of the drug is generally difficult to control following implantation.

Implantable medical devices having thin polymeric coatings containing therapeutic compounds have been described in the art and provide improvements for protecting and controlling the release of drug from the device surface. Some of these coatings are capable of releasing drugs to provide a local therapeutic effect in the vicinity of the implanted device. Such devices have been shown to be particularly valuable for the treatment of diseases of the cardiovascular system.

Drug-eluting stents can provide localized release of a therapeutic substance at the site of administration. Local administration of therapeutic agents via polymeric coatings on stents has shown favorable results in reducing restenosis. Several classes of polymer chemistries have been explored for use in drug-releasing coatings for stent as found in current art, some of which have been approved and are currently being used in medical procedures. Many of these chemistries are useful for delivering hydrophobic drugs.

Drug-releasing coatings are typically prepared using a coating composition having a drug and a polymer dissolved in solvent. The composition is then applied to a substrate surface and the applied material is dried to remove the solvent, which results in a coating of polymeric material with entrapped drug that can be eluted from the coating following implantation.

For example, coating compositions based on poly(alkyl (meth)acrylate) and poly(ethylene-co-vinyl acetate) mixtures suitable for preparing coatings for hydrophobic drugs (such as rapamycin) release are described in U.S. Pat. No. 6,214,901. Release of hydrophobic drugs in a controlled manner can be achieved using this type of polymeric coating system. For example, this system provides sustained and controlled release of the hydrophobic drug, wherein less than 50% of the total quantity of the hydrophilic drug released is released in the first 24 hours.

Another hydrophobic polymer system stated to be useful for drug delivery is described in U.S. Pat. No. 6,669,980, which teaches preparation of medical devices having coatings that include poly(styrene-isobutylene-styrene).

Yet other hydrophobic polymer systems useful for drug delivery are described in U.S. Patent Publication Nos. 2005/0220843 and 2005/0244459.

For certain medical applications, these polymer systems are not ideal. For example, some applications involve the transient insertion of a medical device to a target tissue in the body. For the polymer systems described above, the rate of release of drug from such a polymer system may not be sufficient to provide a therapeutic amount of drug to the target tissue.

In addition, many of the drug delivery coating are made for devices with "static surfaces", that is, surfaces that do not increase in area. Typically, polymer systems that form durable coatings are suitable for these static surfaces. However, on surfaces that are non-static (e.g., elastic surfaces) such durable coatings may not always be appropriate.

SUMMARY OF THE INVENTION

The invention generally relates to insertable medical devices associated with microparticulates containing a bioactive agent. The microparticulates can be released from the device and provide bioactive agent to a subject, and a therapeutic effect at the target site. The devices of the invention have an expandable elastic surface that is associated with the microparticulates via a coated material.

In particular aspects, the invention can be beneficial for transferring a therapeutic quantity of bioactive agent to a target tissue using a transiently insertable medical device, wherein the bioactive agent is released from the microparticulate at the target tissue. Optionally, bioactive agent is associated with a control release component, such as a polymer, to modulate release of the bioactive agent from the microparticulate. The invention provides advantages for the transfer and release of a bioactive agent at a target site.

The devices and methods are advantageous as they minimize loss of bioactive agent during the insertion procedure, which may otherwise occur at locations other than the target tissue. For example, in particular embodiments, the invention provides a balloon catheter wherein the balloon surface is associated with microparticulates according to inventive embodiments described herein. During delivery of the balloon portion to the target tissue (e.g., an intraluminal occlusion) loss of bioactive agent is minimized or eliminated, and transfer of the bioactive agent (via the microparticulates) from the device surface to the target tissue is maximized.

In some aspects, the invention provides an insertable medical device capable of delivering a bioactive agent to a subject, the device including a coating. The device comprises an expandable elastic portion, a coating comprising a flexible hydrogel matrix on the expandable elastic portion, and microparticulates associated with the coating. The microparticulates comprise a bioactive agent that can be released to tissue following insertion of the device and transfer of the microparticulates to the tissue. A portion of the microparticulates associated with the coating are capable of becoming disassociated from the coating upon expansion of the elastic portion in the subject.

In one arrangement, the microparticulates are fully or partially embedded on or near the surface of the flexible hydrogel matrix. In this arrangement, the microparticulates are non-homogenously distributed in the flexible hydrogel matrix.

Upon insertion in a subject, the flexible hydrogel matrix can become more hydrated, resulting in a loosening of the matrix material around the microparticulates. At the target site, the coating can expand along with the elastic portion. The hydration and loosening of the matrix, along with the expansion of the coating, facilitates release of the microparticulates from the coating. The hydration and expansion may also cause the coating to become more porous and force the microparticulates out of the matrix and into tissue.

In some cases, the coating comprises a water-soluble polymer, for example, a water-soluble polymer such as poly(vinylpyrolidone). In some cases, the coating comprises a polymer that is covalently bonded to the surface of the elastic substrate via reacted photogroups. The coating can also be formed from a composition wherein the water-soluble polymer is in macromer form.

In a related aspect, the invention provides a method for delivering a bioactive agent to a subject, using a device including a coating and microparticulates. The method includes a step of providing an insertable medical device, the device comprising an expandable elastic portion, a coating comprising a flexible hydrogel matrix on the surface of the expandable elastic portion, and microparticulates associated with the coating. Another step involves inserting the medical device into a subject, and then expanding the expandable elastic portion at a target site. Upon or after expansion, a portion of the microparticulates become disassociated from the coating and released into tissue at the target site. Bioactive agent can then be released from the microparticulates to provide a therapeutic effect to the subject.

In other aspects of the invention, the insertable medical device includes microparticulates and biodegradable coated material in association with the expandable elastic portion. For instance, in one aspect, the invention provides an insertable medical device capable of delivering a bioactive agent to a subject, the device including a biodegradable coating and microparticulates. The device comprises an expandable elastic portion, a coating comprising a biodegradable polymeric matrix on the expandable elastic portion, and microparticulates associated with the coating. The microparticulates can be fully or partially embedded in biodegradable polymeric matrix. The microparticulates comprise a bioactive agent that can be released following insertion of the device.

In embodiments wherein the device comprises a biodegradable polymeric matrix, at least a portion of the matrix with associated microparticulates is capable of becoming delaminated upon expansion of the elastic portion in the subject. The delaminated biodegradable polymeric matrix with microparticulates adheres to the target tissue. Degradation of the delaminated polymeric matrix and release of the bioactive agent from the microparticulates can occur at the target site.

In another embodiment, the biodegradable polymeric matrix is used in association with a flexible hydrogel matrix. The device comprises an expandable elastic portion, a coating comprising a flexible hydrogel matrix on the expandable elastic portion, a biodegradable polymeric matrix on the flexible hydrogel matrix, and microparticulates associated with the coating. The microparticulates can be arranged so that a significant portion of the microparticulates are partially embedded in the flexible hydrogel matrix and the biodegradable coated material, or a significant portion of the microparticulates are embedded in the biodegradable coated material.

In a related aspect, the invention provides a method for delivering a bioactive agent to a subject, using a device including a coating with a biodegradable polymeric matrix and microparticulates. The method includes a step of providing an insertable medical device, the device comprising coating comprising a biodegradable polymeric matrix in association with the expandable elastic portion, and microparticulates associated with the coating. Another step involves inserting the medical device into a subject, and then expanding the expandable elastic portion in the subject. Upon or after expansion, a portion of the biodegradable polymeric matrix with associated microparticulates becomes delaminated and transferred to the target tissue.

In another aspect, the invention provides an insertable medical device capable of delivering a bioactive agent to a subject, the device including a biodegradable coating and microparticulates, wherein at least a portion of the biodegradable coating erodes and facilitates the release of the microparticulates at the target site. The device comprises an expandable elastic portion, a coating comprising a biodegradable material on the surface of the expandable elastic portion, and microparticulates associated with the biodegradable coating. The microparticulates comprise a bioactive agent that can be released following insertion of the device. At least a portion of the biodegradable coating including the microparticulates is capable of eroding and releasing microparticulates at the target tissue.

In a related aspect, the invention provides a method for delivering a bioactive agent to a subject, using a device including a biodegradable coating and microparticulates. The method includes a step of providing an insertable medical device, the device comprising a biodegradable coating on the expandable elastic portion, and microparticulates associated with the biodegradable coating. Another step involves inserting the medical device into a subject, and then expanding the expandable elastic portion in the subject. During the insertion process, a portion of the biodegradable coating degrades and facilitates release of the microparticulates. In exemplary embodiments, the insertable medical device has an expandable elastic portion that includes a balloon. Such insertable devices include those selected from angioplasty balloons and the like. Angioplasty balloons associated with the inventive microparticulate feature can be used in a process for the treatment of diseased vasculature. Exemplary bioactive agents that can be associated with the microparticulate and released to the vasculature include those selected from the group consisting of antiproliferatives, antiinflamatories, and antiplatelet compounds. An exemplary antiproliferative agent is paclitaxel.

Suitable microparticulates include those formed partially or entirely of a bioactive agent, or more than one bioactive agent.

In some cases the microparticulates include a control release agent. For example, the control release agent can be a biodegradable polymer, such as polymer is selected from the group consisting of PGA, PLA, and PLGA. The biodegradable polymer can be used to provide additional control over release of the bioactive agent, after it has been released from the expanded elastic portion.

DETAILED DESCRIPTION

The embodiments of the present invention described herein are not intended to be exhaustive or to limit the invention to the precise forms disclosed in the following detailed description. Rather, the embodiments are chosen and described so that others skilled in the art can appreciate and understand the principles and practices of the present invention.

All publications and patents mentioned herein are hereby incorporated by reference. The publications and patents disclosed herein are provided solely for their disclosure. Nothing herein is to be construed as an admission that the inventors are not entitled to antedate any publication and/or patent, including any publication and/or patent cited herein.

Generally, the present invention provides methods and devices for the delivery of a bioactive agent to a target tissue using microparticulates. The microparticulates are associated with an expandable elastic surface of an insertable medical device via a coated material. The device can be inserted into a subject to place the expandable elastic surface in contact with a target tissue to which the microparticulates can be transferred. The expandable elastic surface can be expanded, causing release or dissociation of the microparticulates from coating on the surface of the elastic substrate. Alternatively, the expandable elastic surface can include a biodegradable coated material that is released from the elastic surface when the elastic surface is expanded, resulting in the transfer of the biodegradable coated material along with the microparticulates. Following release from the surface of the elastic substrate, the microparticulates can become associated with tissue and release bioactive agent.

Figure 1A:
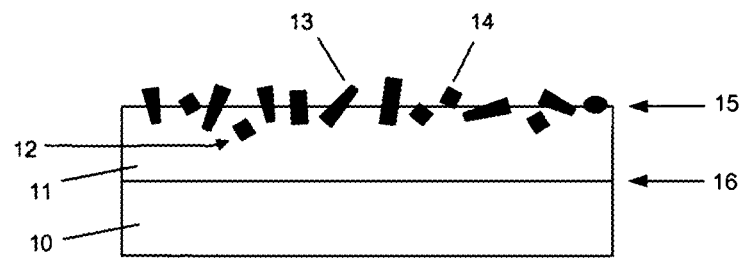
FIGS. 1a-1c are illustrations of a portion of a device having an elastic substrate with a flexible hydrogel coating with embedded microparticulates, and the transfer of the microparticulates from the hydrogel coating to tissue upon expansion of the elastic substrate.

In one embodiment, as shown in FIG. 1a, the device has an expandable elastic substrate 10 (such as a portion of a balloon of a balloon catheter), a flexible hydrogel coating 11, and microparticulates (12, 13, 14) associated with the flexible hydrogel coating. FIG. 1a shows that the microparticulate association is non-homogenous (i.e., the microparticulates are substantially associated with the flexible hydrogel coating 11 near the surface of the flexible hydrogel coating 15, rather predominantly near the flexible hydrogel coating/expandable elastic substrate interface 16, or homogenously distributed in the flexible hydrogel coating. FIG. 1a shows examples of microparticulates that are fully embedded in the flexible hydrogel coating (12), partially embedded in the flexible hydrogel coating (13), and marginally embedded in the flexible hydrogel coating (14). Upon visualization, microparticulates that are marginally embedded in the flexible hydrogel coating may appear to be stuck to the surface of the flexible hydrogel coating.

Figure 1B:
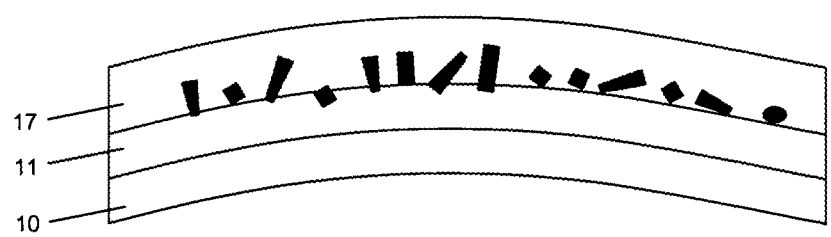

The device (such as in the form of a microparticulate coated catheter balloon) can then be inserted in a subject and delivered to a target site. Upon insertion in a subject, the hydration of the flexible hydrogel matrix increases and the matrix material loosens around the microparticulates. Referring to FIG. 1b, the device is positioned at a target site (e.g., an intraluminal occlusion) where the expandable elastic substrate 10 is expanded, such as by inflation of the balloon, causing it to bulge and push the flexible hydrogel coating 11 up against the tissue 17 of the target site. At the target site, the flexible hydrogel coating 11 expands along with the elastic substrate 10. The hydration and loosening of the flexible hydrogel coating along with the expansion, facilitates release of the microparticulates from the coating 11 into the tissue 17. In some cases, the coating may deform to a point where the microparticulates are no longer entrapped and can be released from the coating. For example, upon expansion, the coating may thin sufficiently to release the microparticulates. Alternatively, or additionally, the coating may expand to a point where pores are created in the expanded coating sufficient in size to release the microparticulates. Microparticulates are transferred to tissue of the subject, and bioactive agent can be released to provide a therapeutic effect.

Figure 1C:
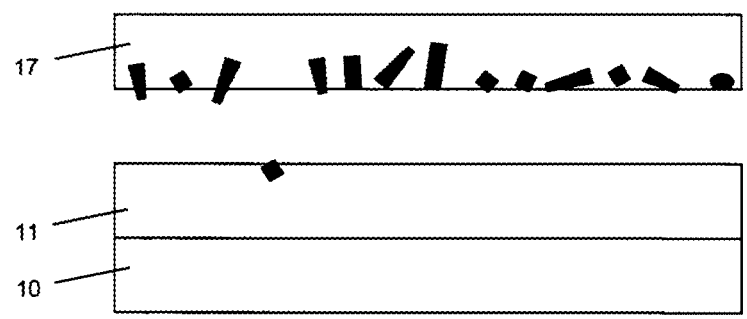

Referring to FIG. 1c, after microparticulate transfer has taken place, the elastic substrate 10 is contracted (e.g., by deflation of the balloon). The expandable elastic substrate 10 and flexible hydrogel coating 11 pulls away from the tissue 17 of the target site, leaving the microparticulates associated with the tissue 17.

FIGS. 1a-1c illustrate an embodiment of the invention and transfer process, with the majority of the microparticulates being transferred from the hydrogel matrix to the tissue. However, the present invention contemplates a transfer of microparticulates to tissue in the range of about 10% to 100%, or more desirably in the range of about 30% to 100%.

The flexible hydrogel matrix can be made from a biostable hydrophilic polymer. The polymer can be covalently bonded to the expandable elastic substrate, covalently bonded to other hydrophilic polymers in the matrix, or both. In some desired aspects, the biostable hydrophilic polymer is bonded to the substrate surface via reacted photogroups.

In other aspects of the invention, the insertable medical device includes a biodegradable coated layer which facilitates association of the microparticulates with the elastic substrate.

The device can comprises a degradable coated layer present between the microparticulates and the surface of the elastic substrate. For example, the degradable coated layer can be present as a base coat on the surface of the elastic substrate. The degradable coated layer can cause association of the microparticulates with the elastic substrate through, for example, adhesive properties of the polymeric materials that are used to form the layer with the microparticulates.

Figure 2A:
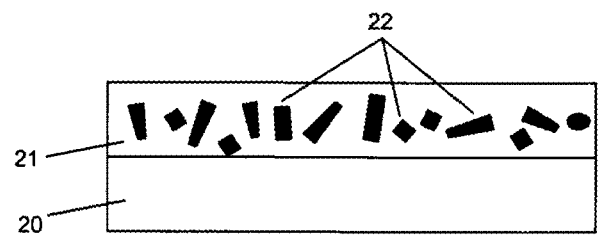
FIGS. 2a-2c are illustrations of a portion of a device having an elastic substrate with a biodegradable coating with embedded microparticulates, and the transfer of fragmented portions of the biodegradable coating with microparticulates to tissue upon expansion of the elastic substrate.

For example, in another aspect, the microparticulates are embedded in, or covered with, a biodegradable coating that is present on the elastic substrate. In a non-expanded state, the microparticulates are substantially or entirely entrapped in the coating, or covered by the coating. FIG. 2a illustrates a device that has an expandable elastic substrate 20 (such as a portion of a balloon of a balloon catheter), a biodegradable coating 21, and microparticulates (22) fully embedded in the biodegradable coating 21.

Figure 2B:
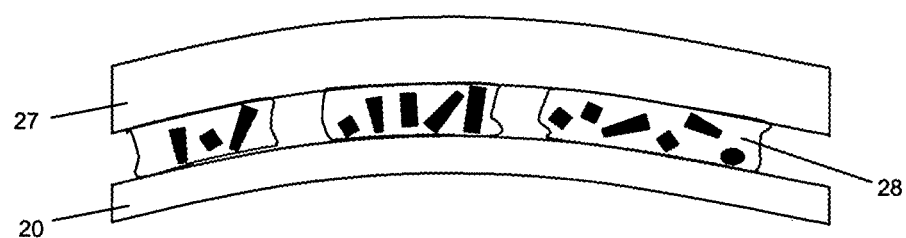

Referring to FIG. 2b, upon expansion of the substrate 20, the biodegradable coating 21 fractures and delaminates from the surface of the substrate 20, thereby causing release of portions of the coating (delaminated biodegradable fragments 28) along with the microparticulates. The delaminated biodegradable fragments 28 with microparticulates is transferred to tissue 27 of the subject. The delaminated biodegradable fragments 28 can have a greater adhesivity to the tissue 27 than to the substrate 20.

Figure 2C:
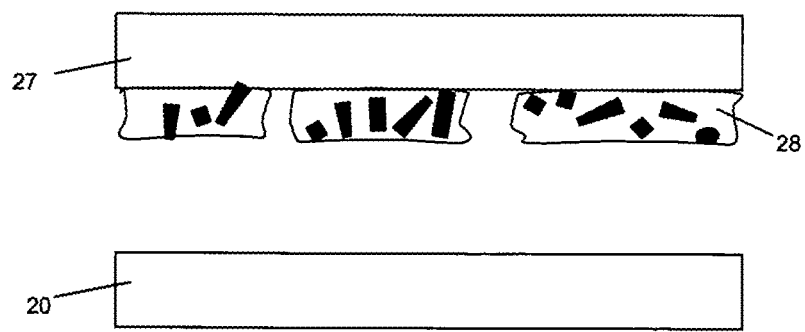

Referring to FIG. 2c, after the transfer has taken place, the elastic substrate 20 is contracted (e.g., by deflation of the balloon). The expandable elastic substrate 20 pulls away from the tissue 27 of the target site, leaving the microparticulates associated with the tissue 27. Bioactive agent can be released from the microparticulates, and the delaminated biodegradable fragments 28 can be degraded.

In some cases the degradable coated layer between the microparticulates and the elastic substrate can erode, facilitating release of the microparticulates. The microparticulates can become released at the target site, along with expansion of the substrate.

Figure 3:
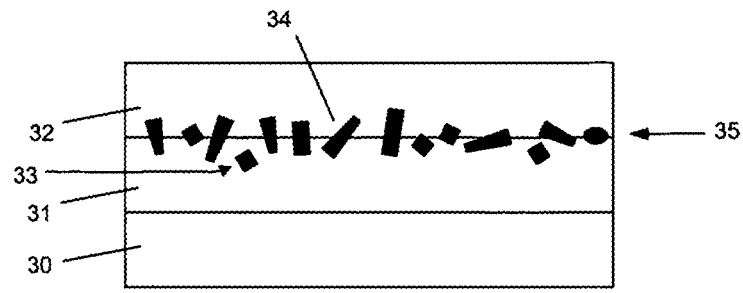
FIGS. 3-5 are illustrations of embodiments showing portions of devices having an elastic substrate with a coating having a flexible hydrogel matrix and a biodegradable polymeric matrix, and embedded microparticulates.
Figure 4:
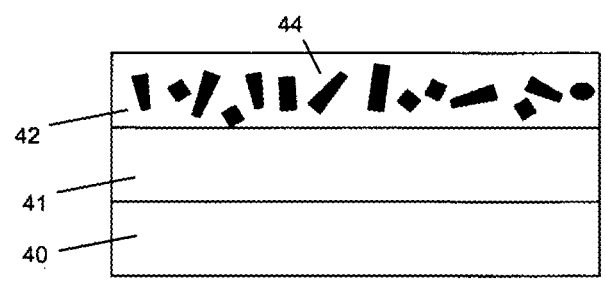
Figure 5:
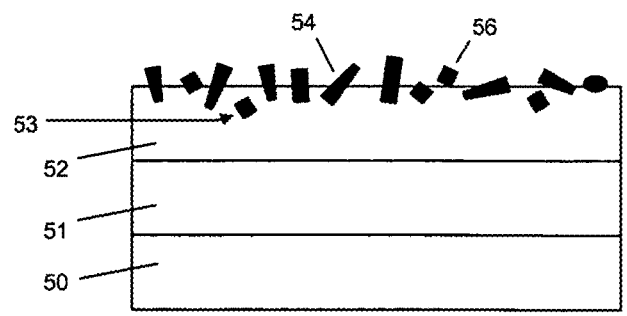

In other embodiments, as illustrated in FIGS. 3-5, the device includes a coating having both a flexible hydrogel matrix and a biodegradable matrix.

For example, as shown in FIG. 3, the device has an expandable elastic substrate 30 (such as a portion of a balloon of a balloon catheter), a coating with a flexible hydrogel layer 31 on the elastic substrate 30, and a biodegradable layer 32 on top of the flexible hydrogel layer 31. In the device of FIG. 3, microparticulates are located in both the flexible hydrogel layer 31 and the biodegradable layer 32, and primarily at the interface 35 between these two layers. Microparticulates can be embedded in the flexible hydrogel layer 31 (e.g., microparticulate 33), as well as by the materials of both the flexible hydrogel layer 31 and the biodegradable layer 32 (e.g., microparticulate 34).

The device of FIG. 4 also has an expandable elastic substrate 40, a coating with a flexible hydrogel layer 41 on the elastic substrate 40, and a biodegradable layer 42. The microparticulates (e.g., microparticulate 44) are primarily located in the biodegradable layer 42, embedded by the biodegradable materials.

The device of FIG. 5 also has an expandable elastic substrate 50, a coating with a flexible hydrogel layer 51 on the elastic substrate 50, and a biodegradable layer 52. In this embodiment, the microparticulates (e.g., microparticulate 44) are primarily associated with the biodegradable layer 42, showing microparticulates that are fully embedded in the biodegradable layer (53), partially embedded in the biodegradable layer (54), and marginally embedded in the biodegradable layer (56).

The coating can be formed on one or more portions of the surface of the elastic substrate. In many aspects the coating is formed over the entire surface of the balloon portion of a balloon catheter. In that manner, when the balloon is expanded in situ, the microparticulates can be transferred to the circumference of the lumen of the artery.

Non-contiguous biodegradable coating patterns are also contemplated. A "non-contiguous" coating refers to a coating material that does not cover the entire elastic surface (e.g., the entire balloon surface), but rather formed at one or more portions of the surface. Non-contiguous coating patterns facilitate delamination of a biodegradable coated material from the elastic surface when it is expanded. In some aspects, a non-contiguous biodegradable coating may experience little or no fracturing before it becomes delaminated from the surface. In other aspects, a non-contiguous biodegradable coating can have a pattern that is easy to fracture, which facilitates delamination. In terms of inflation pressure, non-contiguous biodegradable coatings may require less force for coating delamination.

Figure 6:
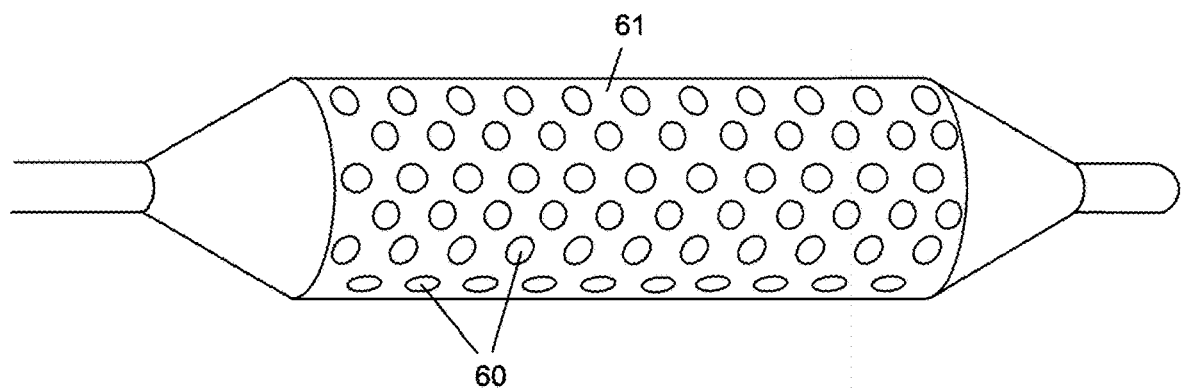
FIG. 6 is an illustration an embodiment showing a non-contiguous dotted coating pattern on the surface of a balloon.
Figure 7:
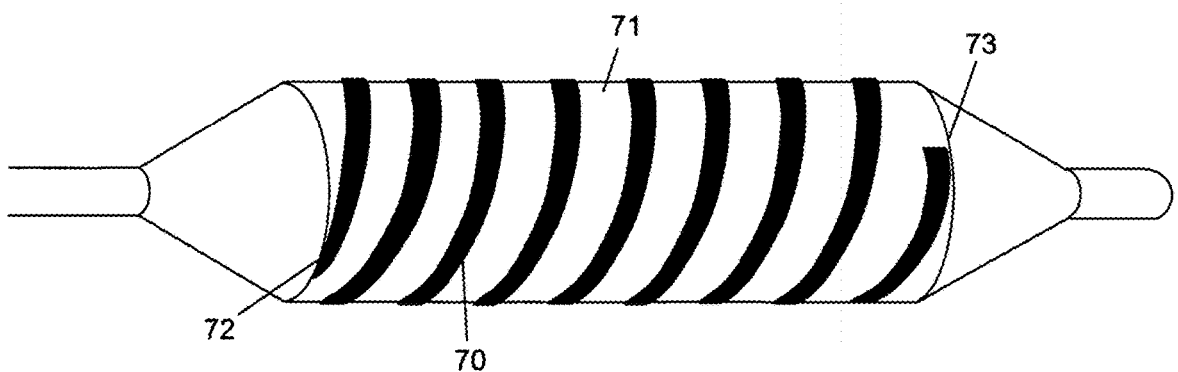
FIG. 7 is an illustration an embodiment showing a non-contiguous helical striped coating pattern on the surface of a balloon.

Examples of non-contiguous biodegradable coatings are shown FIGS. 6 and 7. FIG. 6 shows a non-contiguous biodegradable coating pattern of dots 60 (e.g., "islands") of biodegradable coated material on the elastic surface of a balloon 61. The dots of biodegradable coated material are associated with microparticulates. Upon expansion of the balloon the dots of biodegradable coated material with microparticulates are capable of becoming delaminated from the balloon surface with little or no fracturing, and then can be transferred to tissue. Shapes of such non-contiguous patterns are not limited to circular dots as illustrated, but can include any other shape (polygonal, oval, irregular, etc.).

FIG. 7 shows a non-contiguous biodegradable coating pattern of a circumferential stripe 70 of biodegradable coated material on the surface of the balloon 71. The circumferential stripe may be continuous from a proximal end 72 of the balloon to a distal end 73 (as shown in FIG. 7, which accordingly forms a helical configuration). Alternatively, the pattern can have multiple circumferential stripes, forming rings around the balloon (not shown). Upon expansion of the balloon, biodegradable coated material is easily fractured at multiple locations along its length. The fractured portions are capable of becoming delaminated from the balloon surface, and then can be transferred to tissue.

Biodegradable coatings having non-contiguous patters can be formed directly on the elastic surface of a balloon, or can be formed in association with another coated material, such as a flexible hydrogel layer. Non-contiguous patterns, such as dotted and striped patterns, can be formed using a spray coating apparatus, as described herein.

Figure 8:
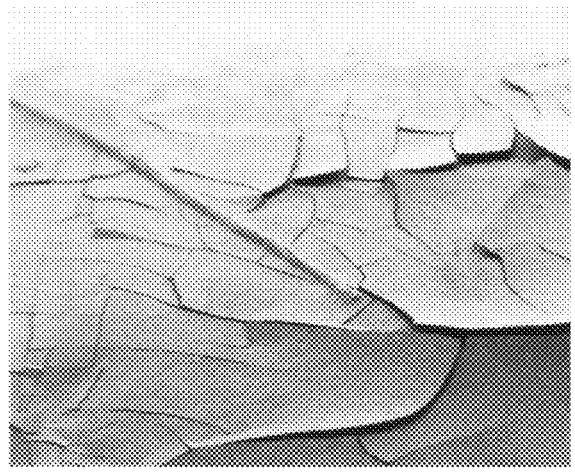
FIG. 8 is a micrograph of a substrate having a delaminated biodegradable coating.
Figure 9:
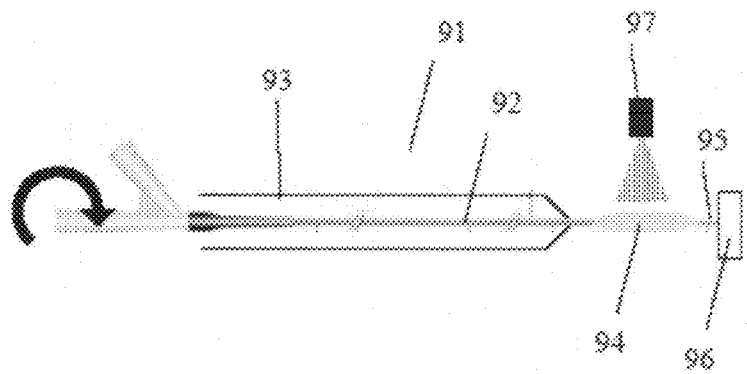
FIG. 9 is an illustration of a coating apparatus with a mounted balloon catheter.

A representative micrograph of a delaminated coating is shown in FIG. 8.

The present invention contemplates various types of insertable medical devices, which include an expandable elastic substrate from which the microparticulates can be released. In one embodiment, the insertable medical device that comprises an elastic substrate with microparticulates is a balloon catheter. Balloon catheters are commonly used in angioplasty procedures for the treatment of arteries that are diseased. Balloon angioplasty generally involves the dilation or reopening of blocked intraluminal channels. Balloon catheters with the inventive microparticulate associated surfaces will be described in more detail herein.

The expandable elastic portion of the device can be formed from any material, or combination of materials, capable of expanding, and suitable for use within the body. The one or more material(s) can be based on use of the device. In many aspects the expandable elastic materials are compliant and flexible materials, such as elastomers (polymers with elastic properties). Elastomers are typically thermoplastic polymers. Exemplary elastomers can be formed from various polymers including polyurethanes and polyurethane copolymers, polyethylene, styrene-butadiene copolymers, polyisoprene, isobutylene-isoprene copolymers (butyl rubber), including halogenated butyl rubber, butadiene-styrene-acrylonitrile copolymers, silicone polymers, fluorosilicone polymers, polycarbonates, polyamides, polyesters, polyvinyl chloride, polyether-polyester copolymers, and polyether-polyamide copolymers.

The expandable elastic portion can be made of a single elastomeric material, or a combination of materials. The expandable elastic portion can be manufactured by an extrusion process, so that the elastic portion is a single layer of material, or co-extruded to form a multi-layered material.

The elastic portion can have a thickness suitable for the desired application and device. For example, the thickness of an elastic portion can be in the range of about 5 µm to about 100 µm.

Exemplary thicknesses for the walls of catheter balloons are in the range of about 5 µm to about 20 µm. The actual thickness of the balloon wall may depend on one or more factors, such as the desired pliability of the balloon, the overall profile of the balloon on the catheter (low profile devices may use thin walled balloons), the pressure rating for the balloon wall, or the expansion properties of the balloon. In some cases, a balloon with a thin wall is used, so as to accommodate the increase in thickness when a coating with microparticulates is formed on the surface.

The manufacture of expandable elastic substrates is well known in the art, and any suitable process can be carried out to provide the expandable substrate portion of the insertable medical device as described herein. Catheter balloon construction is described in various references, for example, U.S. Pat. Nos. 4,490,421, 5,556,383, 6,210,364, 6,168,748, 6,328,710, and 6,482,348. Molding processes are typically performed for balloon construction. Balloons fabricated by such processes are suitable as substrates for the microparticulate and coated materials according to the present invention. In an exemplary molding process, an extruded polymeric tube is radially and axially expanded at elevated temperatures within a mold having the desired shape of the balloon. The balloon can be subjected to additional treatments following the molding process. For example, the formed balloon can be subjected to additional heating steps to reduce shrinkage of the balloon.

According to the invention, the microparticulates are the particulate components that include bioactive agent, and which are releasable from the elastic surface of the device. The microparticulates can be any three-dimensional particle of size and shape sufficient to be associated with the elastic substrate via coating materials, and then dissociated upon its expansion of the substrate.

Many microparticulates have a spherical, or substantially spherical shape, such as those that are formed from synthetic polymeric materials. In many aspects, the elastic portion of the device is associated with spherical or substantially spherical microparticulates, which are herein referred to as "microspheres."

However, microparticulates can be used that have noticeably non-spherical shapes or irregular shapes (for example, when examined by microscopy). For example, the microparticulates can have curved surfaces, flat surfaces, or combinations thereof. If desired, the expandable elastic portion can be associated with a plurality of microparticulates of a combination of different sizes and/or shapes.

Microparticulates can be in the form of microcrystals or particles that otherwise have crystalline shapes or configurations. Microparticulates with crystalline shapes may be composed of bioactive agent molecules that are arranged in the microparticulates in an orderly repeating pattern extending in all three spatial dimensions. Crystalline shapes can typically be observed under the microscope. Microcrystals may be observed as having rod-like, filament-like, sliver-like, or needle-like shapes.

In association with the coating on the elastic substrates, microparticulates may also be observed (or exist in) as aggregated or clumped structures. For example, aggregates of microparticulates having rod-like, filament-like, sliver-like, or needle-like shapes can be associated with the coating materials.

In many aspects, microparticulates associated with the expandable elastic portion have a greatest average dimension that is less than about 50 µm. For example, microparticulates can have an elongated shape, with a length along the elongate axis of less than about 50 µm. Size analysis, such as by microscopy, can be used to assess irregular shaped microparticulates or microcrystals. In some cases, the microparticulates have a greatest average dimension in the range of about 100 nm to about 50 µm, about 100 nm to about 25 µm, about 100 nm to about 20 µm, or about 100 µm to about 10 µm.

Also, in many aspects, the microparticulates have a spherical or substantially spherical shape with an average diameter of about 100 nm or larger. For example, the microparticulates associated with the expandable elastic portion can have an average diameter in the range of about 100 nm to about 50 µm, about 150 nm to about 25 µm, about 200 nm to about 20 µm, or about 0.3 µm to about 10 µm.

In many aspects, microparticulates associated with the expandable elastic portion have an average diameter ("dn", number average) that is less than about 50 µm. Also, in many aspects, the microparticulates can have an average diameter of about 100 nm or larger. For example, the microparticulates associated with the expandable elastic portion can have an average diameter in the range of about 100 nm to about 50 µm, about 150 nm to about 25 µm, about 200 nm to about 20 µm, or about 0.3 µm to about 10 µm.

Depending on the manner by which the microparticulates are associated with the elastic portion, it can be desirable to use microparticulates within a particular size range. For example, when the microparticulates are immobilized in a coating on the surface of the elastic portion, it is generally desirable to utilize microparticulates having an average diameter that is smaller than the thickness of the coating.

In some aspects, the microparticulates associated with the elastic surface can also have a low size polydispersity. Low size dispersity means that there is little variation in the size of the microparticulates in the population of microparticulates (as compared to a high size dispersity, which means that there is considerable variation in the size of the microparticulate population).

In the least, the microparticulates that are associated with the expandable elastic substrate include a bioactive agent. In some embodiments, the microparticulates can be formed completely or substantially of a selected bioactive agent for treatment or prevention of a condition. In other embodiments, the microparticulates can be formed from a combination of bioactive agents (e.g., two or more different bioactive agents). In other embodiments, the microparticulates can be formed from a bioactive agent and another component that is not intended to provide a therapeutic effect to the subject, such as a polymer that can modulate the release of the bioactive agent from the microparticulates. In other embodiments the microparticulates include two or more components, such as two or more polymers that modulate the release of the bioactive agent from the microparticulate.

Components of the microparticulate can be in mixture with one another in a portion of, or all of, the microparticulate. Alternatively, the components can be entirely or substantially separated from one another in the microparticulate. For example, the microparticulate can be formed comprising a substantially homogenous mixture of a bioactive agent and a release-modulating polymer. As another example, the microparticulate can be formed comprising a bioactive agent core and a release-modulating polymer shell around the core.

The term "bioactive agent," refers to an inorganic or organic molecule, which can be synthetic or natural that causes a biological effect when administered in vivo to an animal, including but not limited to birds and mammals, including humans. A partial list of bioactive agents is provided below. One may choose any one of the bioactive agents to be included in a microparticulate set alone, or in combination with any other bioactive agent. A comprehensive listing of bioactive agents, in addition to information of the water solubility of the bioactive agents, can be found in *The Merck Index*, Thirteenth Edition, Merck & Co. (2001).

The microparticulates, which are released from the elastic substrates, can be used to deliver bioactive agents falling within one or more of the following classes, which include, but are not limited to, ACE inhibitors, actin inhibitors, analgesics, anesthetics, anti-hypertensives, antipolymerases, antisecretory agents, antibiotics, anti-cancer substances, anti-cholinergics, anti-coagulants, anti-convulsants, anti-depressants, anti-emetics, antifungals, anti-glaucoma solutes, antihistamines, antihypertensive agents, anti-inflammatory agents (such as NSAIDs), antimetabolites, antimitotics, antioxidizing agents, anti-parasite and/or anti-Parkinson substances, antiproliferatives (including antiangiogenesis agents), anti-protozoal solutes, anti-psychotic substances, anti-pyretics, antiseptics, anti-spasmodics, antiviral agents, calcium channel blockers, cell response modifiers, chelators, chemotherapeutic agents, dopamine agonists, extracellular matrix components, fibrinolytic agents, free radical scavengers, growth hormone antagonists, hypnotics, immunosuppressive agents, immunotoxins, inhibitors of surface glycoprotein receptors, microtubule inhibitors, miotics, muscle contractants, muscle relaxants, neurotoxins, neurotransmitters, polynucleotides and derivatives thereof, opioids, prostaglandins, remodeling inhibitors, statins, steroids, thrombolytic agents, tranquilizers, vasodilators, and vasospasm inhibitors.

In some aspects the microparticulates comprise an antiproliferative agent. The antiproliferative agent can be an anti-angiogenesis agent.

In some aspects the microparticulates comprise an anti-inflammatory agent.

In some aspects the microparticulates comprise a cell response modifier.

In some aspects the microparticulates comprise an anti-thrombotic agent.

In some aspects the microparticulates comprise an immunosuppressive agent.

Cell response modifiers are chemotactic factors such as platelet-derived growth factor (pDGF). Other chemotactic factors include neutrophil-activating protein, monocyte chemoattractant protein, macrophage-inflammatory protein, SIS (small inducible secreted) proteins, platelet factor, platelet basic protein, melanoma growth stimulating activity, epidermal growth factor, transforming growth factor (alpha), fibroblast growth factor, platelet-derived endothelial cell growth factor, insulin-like growth factor, nerve growth factor, vascular endothelial growth factor, bone morphogenic proteins, and bone growth/cartilage-inducing factor (alpha and beta). Other cell response modifiers are the interleukins, interleukin inhibitors or interleukin receptors, including interleukin 1 through interleukin 10; interferons, including alpha, beta and gamma; hematopoietic factors, including erythropoietin, granulocyte colony stimulating factor, macrophage colony stimulating factor and granulocyte-macrophage colony stimulating factor; tumor necrosis factors, including alpha and beta; transforming growth factors (beta), including beta-1, beta-2, beta-3, inhibin, activin, and DNA that encodes for the production of any of these proteins.

Examples of statins include lovastatin, pravastatin, simvastatin, fluvastatin, atorvastatin, cerivastatin, rosuvastatin, and superstatin.

Examples of steroids include glucocorticoids such as cortisone, hydrocortisone, dexamethasone, betamethasone, prednisone, prednisolone, methylprednisolone, triamcinolone, beclomethasone, fludrocortisone, and aldosterone; sex steroids such as testosterone, dihydrotestosterone, estradiol, diethylstilbestrol, progesterone, and progestins.

The bioactive agent can provide antirestenotic effects, such as antiproliferative, antiplatelet, and/or antithrombotic effects. In some embodiments, the bioactive agent can be selected from anti-inflammatory agents, immunosuppressive agents, cell attachment factors, receptors, ligands, growth factors, antibiotics, enzymes, nucleic acids, and the like. Compounds having antiproliferative effects include, for example, actinomycin D, angiopeptin, c-myc antisense, paclitaxel, taxane, and the like.

Representative examples of bioactive agents having antithrombotic effects include heparin, heparin derivatives, sodium heparin, low molecular weight heparin, hirudin, lysine, prostaglandins, argatroban, forskolin, vapiprost, prostacyclin and prostacyclin analogs, D-phe-pro-arg-chloromethylketone (synthetic antithrombin), dipyridamole, glycoprotein IIb/IIIa platelet membrane receptor antibody, coprotein IIb/IIIa platelet membrane receptor antibody, recombinant hirudin, thrombin inhibitor (such as commercially available from Biogen), chondroitin sulfate, modified dextran, albumin, streptokinase, tissue plasminogen activator (TPA), urokinase, nitric oxide inhibitors, and the like.

The bioactive agent can also be an inhibitor of the GPIIb-IIIa platelet receptor complex, which mediates platelet aggregation. GPIIb/IIIa inhibitors can include monoclonal antibody Fab fragment c7E3, also known as abciximab (ReoPro™), and synthetic peptides or peptidomimetics such as eptifibatide (Integrilin™) or tirofiban (Agrastat™).

The bioactive agent can be an immunosuppressive agent, for example, cyclosporine, CD-34 antibody, everolimus, mycophenolic acid, sirolimus, tacrolimus, and the like.

Additionally, the bioactive agent can be a surface adhesion molecule or cell-cell adhesion molecule. Exemplary cell adhesion molecules or attachment proteins, such as extracellular matrix proteins, include fibronectin, laminin, collagen, elastin, vitronectin, tenascin, fibrinogen, thrombospondin, osteopontin, von Willibrand Factor, bone sialoprotein (and active domains thereof), and hydrophilic polymers such as hyaluronic acid, chitosan and methyl cellulose, and other proteins, carbohydrates, and fatty acids. Other cell-cell adhesion molecules include N-cadherin and P-cadherin and active domains thereof.

Microparticulates that are formed solely of one or more bioactive agents can be associated with the expandable elastic substrate and released to target tissue in vivo. In other words, the microparticulates can be formed substantially or entirely of one or more bioactive agents. An excipient substance that may otherwise control release of the bioactive agent from the microparticulates is not required. This can be important in many therapeutic methods, as the amount of bioactive agent that is available to a subject following administration of the microparticulates can be maximized. This is also advantageous for applications involving the site-specific delivery of bioactive agents, or the delivery of bioactive agents to a limited access region in the body. As another advantage, the amount of secondary materials present in and capable of being released from the microparticulate can be minimized.

Microparticulates formed solely of one or more bioactive agents have been described in the art. A microparticulate that is formed entirely or almost entirely (e.g., allowing for trace amounts of one or more other components) of a bioactive agent is referred to herein as a "neat" microparticulate.

For example, the preparation of paclitaxel microparticles has been described in U.S. Pat. No. 6,610,317. Therefore, in some aspects of the invention, the microparticulates are composed of a low molecular weight bioactive agent.

Other techniques for the preparation of microparticulates are known in the art and include precipitation and crystallization. For example, a liquid composition of a bioactive agent in a solvent (e.g., an organic solvent) can be precipitated by addition of an excess of a non-solvent (e.g., water or an aqueous composition). The solvent can be removed from the liquid composition by phase separation, or a comparable technique. The precipitated composition can then be subjected to comminution, which refers to mechanical process that can reduce the size of the precipitated particulates. For example, wet milling can be used to reduce particle size in a liquid composition and produce microparticulates. The precipitated bioactive agent can then be filtered and washed with the non-solvent.

Another process that can be used for the preparation of microparticulates is spray drying. A liquid composition of the bioactive agent and solvent can be atomized and spray deposited on a substrate, and during the process the solvent is evaporated from the droplets. The concentration of the bioactive agent, the droplet size, and the evaporation of the solvent can be determined to provide desired microparticulate formation.

In some modes of preparing the coating, a spray drying process is performed by directly spraying a liquid composition of the bioactive agent onto a coated layer (for example, the flexible hydrogel layer or a biodegradable material layer) of the device. In this process, the microparticulates are formed on the coated layer as the solvent from the droplets evaporates. The sprayed composition may also include a liquid that causes the swelling of the hydrogel layer. Therefore, as the microparticulates form they also move into the hydrogel material. As the non-solvent evaporates, the hydrogel shrinks and the microparticulates become constrained by the hydrogel material and at least partially embedded in the flexible hydrogel coating (referring back to FIG. 1a).

As another example, therapeutic Fab (antibody) fragment microspheres, are described in commonly-assigned U.S. provisional patent application No. 60/937,492, filed Jun. 28, 2007 to Slager, et al. Therefore, in another aspect of the invention, the microparticulates are composed of higher molecular weight bioactive agents, such as polypeptides.

Excipients are a class of components that can optionally be included in the microparticulates. Excipients can improve the stability of the bioactive agent within the microparticulate, or can change physical properties of the microparticulates. Exemplary excipients include glycerol, diethylene glycol, sorbitol, sorbitol esters, maltitol, sucrose, fructose, invert sugars, corn syrup, and mixtures thereof. The amount and type of excipient(s) can be based on known standards and techniques. Antioxidants can optionally be added to the microparticulates, such as to improve the stability of the bioactive agent.

Imaging components can also be included in the microparticulates. The imaging components can be detectable using common imaging techniques and suitable for use in the inventive methods. These agents can be capable of allowing imaging of a desired site in the body, e.g., an intravascular target site, before, during or after release of the microparticulates from the elastic substrate. Examples of imaging agents include substances having a label that is detectable in vivo, e.g., antibodies attached to fluorescent labels, paramagnetic materials, such as iron oxide, Gd, or Mn, or a radioisotope. Imaging components can be detected by paramagnetic resonance imaging, ultrasonic imaging, or other suitable detection techniques.

The bioactive agent-containing microparticulates can optionally include one or more release control components to modulate release of the bioactive agent from the microparticulate. In some aspects, the release control component is a material present in the microparticulate that erodes, dissolves, and/or degrades after the microparticulates are in contact with body fluid or tissue. The erosion, dissolution, or degradation of one or more components can slow the release of bioactive agent from the microparticulate so the bioactive agent is present in more therapeutically effective amounts over a desired period of treatment.

In some aspects, the microparticulates comprise a bioactive agent and one or more degradable or erodable polymers (herein referred to as "degradable polymers"). As used herein, biodegradable polymers are capable of being broken down by various enzymes, such as those in the normal functioning of the human body and living organisms (such as bacteria) and/or in water environments (by simple hydrolysis). Once broken down, the degradation products of these polymers are gradually absorbed or eliminated by the body. The degradable polymers can be natural or synthetic, or can be composed of natural and synthetic blocks. The choice of the degradable polymer components in the microparticulate can be chosen based on the present disclosure, as well as knowledge available to one of skill in the art.

In some modes of practice, the degradable polymer is synthetic. Exemplary synthetic degradable polymers can be selected from the group of polyesters such as poly(lactic acid) (poly(lactide)), poly(glycolic acid) (poly(glycolide)) poly(lactide-co-glycolide), poly(dioxanone); polylactones such as poly(caprolactone) and poly(valerolactone), copolymers such as poly(glycolide-co-polydioxanone), poly(glycolide-co-trimethylene carbonate), and poly(glycolide-co-caprolactone); poly(3-hydroxybutyrate), poly(3- hydroxyvalerate), poly(tartronic acid), poly(β-malonic acid), poly(propylene fumarate); degradable polyesteramides; degradable polyanhydrides and polyalkeneanhydrides (such as poly(sebacic acid), poly(1,6-bis(carboxyphenoxy)hexane), poly(1,3-bis(carboxyphenoxy)propane); degradable polycarbonates and aliphatic carbonates; degradable polyiminocarbonates; degradable polyarylates; degradable polyorthoesters; degradable polyurethanes; degradable polyphosphazenes; degradable polyhydroxyalkanoates; and degradable polyamides.

Exemplary biodegradable poly(ester-amides) are described in U.S. Pat. No. 6,703,040. These poly(ester-amides) can be formed by the polymerization of a diol (D), a dicarboxylic acid (C) and an alpha-amino acid (A) through ester and amide links in the form $(DACA)_n$.

Biodegradable polyetherester copolymers can also be used. Generally speaking, the polyetherester copolymers are amphiphilic block copolymers that include hydrophilic (for example, a polyalkylene glycol, such as polyethylene glycol (PEG)) and hydrophobic blocks (for example, polyethylene terephthalate). Examples of block copolymers include poly (ethylene glycol)-based and poly(butylene terephthalate)-based blocks (PEG/PBT polymer). Examples of these types of multiblock copolymers are described in, for example, U.S. Pat. No. 5,980,948. PEG/PBT polymers are commercially available from Octoplus BV (Leiden, Netherlands), under the trade designation PolyActive™.

Other PEG-containing block copolymers, such as those including one or more polymeric blocks selected from poly(hydroxybutyrate) (PHB), poly(oxyethylene) (POE), poly(caprolactone) (PCL), and poly(lactide) (PLA) are available from Advanced Polymer Materials, Inc. (Lachine, QC, Canada).

Biodegradable copolymers having a biodegradable, segmented molecular architecture that includes at least two different ester linkages can also be used. The biodegradable polymers can be block copolymers (of the AB or ABA type) or segmented (also known as multiblock or random-block) copolymers of the $(AB)_n$ type. These copolymers are formed in a two (or more) stage ring opening copolymerization using two (or more) cyclic ester monomers that form linkages in the copolymer with greatly different susceptibilities to transesterification. Examples of these polymers are described in, for example, U.S. Pat. No. 5,252,701 (Jarrett et al., "Segmented Absorbable Copolymer").

Other exemplary multi-block copolymers have a structure according to any of the formulae (1)-(3) as described in EP 1555278:

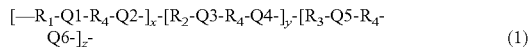
(1)

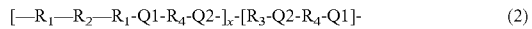
(2)

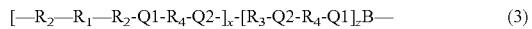
(3)

In these formulas, $R_1$ and $R_2$ can be an amorphous polyester, amorphous polyetherester or amorphous polycarbonate; or an amorphous pre-polymer that is obtained from combined ester, ether and/or carbonate groups. $R_1$ and $R_2$ can contain polyether groups, which may result from the use of these compounds as a polymerization initiator, the polyether being amorphous or crystalline at room temperature. However, the polyether thus introduced will become amorphous at physiological conditions. $R_1$ and $R_2$ are derived from amorphous pre-polymers or blocks A and B, respectively, and $R_1$ and $R_2$ are not the same. $R_1$ and $R_2$ can contain a polyether group at the same time, but it is preferred that only one of them contains a polyether group. "z" is zero or a positive integer. $R_3$ is a polyether, such as poly(ethylene glycol), and may be present (z≠0) or not (z=0). $R_3$ will become amorphous under physiological conditions. $R_4$ is an aliphatic $C_2$-$C_8$ alkylene group, optionally substituted by a $C_1$-$C_{10}$ alkylene, the aliphatic group being linear or cyclic, wherein $R_4$ is preferably a butylene, —$(CH_2)_4$-group, and the $C_1$-$C_{10}$ alkylene side group may contain protected S, N, P or O moieties. "x" and "y" are both positive integers, which are both preferably at least 1, whereas the sum of "x" and "y" (x+y) is preferably at most 2000, more preferably at most 500, most preferably at most 200. Q1-Q6 are linking units obtained by the reaction of the pre-polymers with the multifunctional chain-extender. Q1-Q6 are independently amine, urethane, amide, carbonate, ester or anhydride.

Other suitable biodegradable polymer materials include biodegradable terephthalate copolymers that include a phosphorus-containing linkage. Polymers having phosphoester linkages, called poly(phosphates), poly(phosphonates) and poly(phosphites), are known. See, for example, Penczek et al., Handbook of Polymer Synthesis, Chapter 17: "Phosphorus-Containing Polymers," 1077-1132 (Hans R. Kricheldorf ed., 1992), as well as U.S. Pat. Nos. 6,153,212, 6,485,737, 6,322,797, 6,600,010, and 6,419,709. Biodegradable terephthalate polyesters can also be used that include a phosphoester linkage that is a phosphite. Suitable terephthalate polyester-polyphosphite copolymers are described, for example, in U.S. Pat. No. 6,419,709 (Mao et al., "Biodegradable Terephthalate Polyester-Poly(Phosphite) Compositions, Articles, and Methods of Using the Same). Biodegradable terephthalate polyester can also be used that include a phosphoester linkage that is a phosphonate. Suitable terephthalate polyester-poly(phosphonate) copolymers are described, for example, in U.S. Pat. Nos. 6,485,737 and 6,153,212 (Mao et al., "Biodegradable Terephthalate Polyester-Poly(Phosphonate) Compositions, Articles and Methods of Using the Same). Biodegradable terephthalate polyesters can be used that include a phosphoester linkage that is a phosphate. Suitable terephtalate polyester-poly(phosphate) copolymers are described, for example, in U.S. Pat. Nos. 6,322,797 and 6,600,010 (Mao et al., "Biodegradable Terephthalate Polyester-Poly(Phosphate) Polymers, Compositions, Articles, and Methods for Making and Using the Same).

Biodegradable polyhydric alcohol esters can also be used (see, for example, U.S. Pat. No. 6,592,895). This patent describes biodegradable star-shaped polymers that are made by esterifying polyhydric alcohols to provide acyl moieties originating from aliphatic homopolymer or copolymer polyesters. The biodegradable polymer can be a three-dimensional crosslinked polymer network containing hydrophobic and hydrophilic components that form a hydrogel with a crosslinked polymer structure, such as that described in U.S. Pat. No. 6,583,219. The hydrophobic component is a hydrophobic macromer with unsaturated group terminated ends, and the hydrophilic polymer is a polysaccharide containing hydroxy groups that are reacted with unsaturated group introducing compounds. Other suitable biodegradable polymers can comprise a polymer based upon α-amino acids (such as elastomeric copolyester amides or copolyester urethanes, as described in U.S. Pat. No. 6,503,538).

Degradable polymers can also include dextran-based polymers such as those described in U.S. Pat. No. 6,303,148. Exemplary dextran based degradable polymers including those available commercially under the tradename OCTODEX™.

Other biodegradable polymers include polymethylidenemalonate, polyhydroxybutyrate, and the like.

The microparticulates can also be formed using natural biodegradable polysaccharides. Natural biodegradable polysaccharides having pendent coupling groups, such as polymerizable groups, can be reacted to form a body member with a cross-linked matrix of polysaccharides. Desirably, the natural biodegradable polysaccharides are low molecular weight polymers, such as having a molecular weight of about 50,000 Da or less, 25,000 Da or less, or 10,000 Da or less.

Natural biodegradable polysaccharides with pendent coupling groups are described in U.S. Pub. No. 2005/0255142, published Nov. 17, 2005, (Chudzik et al.) and U.S. patent application Ser. No. 11/271,213, filed Nov. 11, 2005 (Chudzik et al.), both commonly assigned to the applicant of the present invention. One preferred class of natural biodegradable polysaccharides are selected from the group of maltodextrin, amylose, and polyalditol.

The microparticulates can also be formed using polysaccharides derivatized with hydrophobic moieties. Exemplary hydrophobic polysaccharides can be prepared according to methods described in U.S. Pub. No. 2007/0260054, Nov. 8, 2007 (Chudzik, S. J.), and assigned to the applicant of the present invention. The body member can be formed using a hydrophobic moiety derivatized with hydrophobic moieties comprising a $C_2$-$C_{18}$, linear, branched, or cyclic alkyl group, or a $C_2$-$C_{10}$, or a $C_2$-$C_6$, linear, branched, or cyclic alkyl group. In some aspects, the hydrophobic derivative of a natural biodegradable polysaccharide has a degree of substitution of greater than 1.

Degradable microparticulates can be prepared incorporating various biologically active agents by established techniques, for example, the solvent evaporation technique (see, for example, Wiehert, B. and Rohdewald, P. J Microencapsul. (1993) 10:195).

In some aspects, the microparticulates include two or more synthetic biodegradable polymers, one of which delays release of the bioactive agent from the microparticulate. Selection of a first and second biodegradable polymer can be performed based on known or calculated rates of degradation of selected polymers.

In one mode of practice, the microparticulate comprises a first biodegradable polymer that has a faster rate of degradation than a second polymer. The second polymer, which is more slowly degrading, reduces the rate of release of the bioactive agent from the matrix. Additional polymers may optionally be included in the microparticulates. For example, the microparticulates can include a third, fourth, fifth polymer, etc.

In some cases, selection of first and second biodegradable polymers can be performed based on known or calculated glass transition temperatures (Tg) of selected polymers. Tg is the specific temperature at which a polymer transitions from a glassy state to a rubbery state. Tg is an inherent, physical property of polymers that can be obtained from the technical literature (for example, see Thermal Analysis of Polymeric Materials Wunderlich, B. (2005) Springer, Berlin; or Handbook of Polymer Synthesis, Kricheldorf et al. (2005) Marcel Dekker, New York) or determined using analytical techniques such as differential scanning calorimetry (DSC), or by mathematical techniques such as the Fox equation Fox, T. G. (1956) *Bull. Am. Physics Soc.* 1, 3, p. 123.

In one mode of practice, the microparticulate comprises a first polymer that has a lower Tg than a second polymer. The second polymer, which is harder, can reduce the rate of release of the bioactive agent from the matrix. For example, the Tg of a suitable first polymer such as PLGA is about 45° C., and the Tg of a suitable second polymer such as PLLA is about 55° C.

In some aspects the difference between the Tg of the first and second polymer is about 5° C. or greater. In more specific aspects the difference between the Tg of the first and second polymer is about 10° C. or greater.

In some aspects, the first and second polymers have Tgs of about 35° C. or greater. In more specific aspects the first and second polymers have Tgs in the range of about 35° C. to about 65° C.

Selection of the first and second polymers can also be based on other properties of the polymers such as molecular weight, solubility, and rheology.

In some aspects, the microparticulate includes a bioactive agent and a polymer, wherein the microparticulate has a structure that comprises an inner portion comprising the bioactive agent and an outer portion comprising polymer. For example, the microparticulate can have a bioactive agent core and polymer shell.

In some aspects, the core of the microparticulate is formed substantially or entirely of bioactive agent, and the shell comprises a biodegradable polymer.

In some aspects, the core of the microparticulate is comprises a bioactive agent and a first polymer, and the shell comprises a second polymer, such as a biodegradable polymer. For example, the first and second polymers are selected from synthetic biodegradable polymers.

The inner portion (e.g., core) of the microparticulate includes at least most of, if not all, of the bioactive agent present in the microparticulate. Various techniques can be used to prepare microparticulates having inner and outer portions (see, for example, Pekarek, K. J. (1994) Nature 367:258-60). Some techniques are based on phase separation of a polymer mixture. Many phase separation techniques also involve solvent evaporation.

Microparticulates comprising an inner portion and an outer portion can be prepared by first preparing a first composition that includes the first polymer and the bioactive agent. The first composition can be treated to provide a homogenous suspension of the first polymer and the bioactive agent. The homogenized first composition can then be combined with a second composition that includes the second polymer. The mixture of the first and second compositions can then be homogenized. After these steps microparticulates can be formed by combining the composition with a solution that promotes formation of the microparticulate, such as a polyvinylalcohol-containing solution. In one mode of practice, the microparticulates can then be recovered by, for example, centrifugation, and then optionally washed, and frozen or lyophilized.

In some specific aspects, the inner portion of the microparticulates comprise a synthetic biodegradable copolymer, such as poly(lactide-co-glycolide) and an outer portion of the microparticulates comprise a synthetic biodegradable homopolymer, such as poly(lactide).

The microparticulates can also include one or more non-polymeric compounds to control release of the bioactive agent. For example, the microparticulates can include a soluble metal or metal salt to control release of the bioactive agent. Exemplary metal salts inorganic metal chlorides, fluorides, and oxides. The metal salt can be slightly soluble in water. The microparticulates can be partially or wholly coated with a metal salt.

In some aspects the elastic surface is associated with two or more sets of microparticulates. The use of two or more sets of microparticulates may allow a particular bioactive agent to be released at different rates after the microparticulates have been transferred to tissue, or may allow two different types of bioactive agents to be released to a subject. For example, a first bioactive agent can be released from a first set of microparticulates and a second bioactive agent can be released from a second set of microparticulates.

Two sets of microparticulates can be used if it is desired to deliver two bioactive agents which are mutually incompatible in a particular environment, for example, as hydrophobic and hydrophilic drugs are incompatible in either a polar or non-polar solvent. For example, the first bioactive agent can be a hydrophobic drug present in a first set of microparticulates, and the second bioactive agent can be a hydrophilic drug present in a second set of microparticulates. Useful degradable polymers or degradable copolymers for hydrophobic drugs have a high lactide or high caprolactone content; whereas useful degradable polymers or degradable copolymers for hydrophilic drugs have high glycolide content.

In one aspect of the invention, the microparticulates are at least partially embedded in a coating that is present on the elastic substrate, wherein the coating is in a non-expanded state and has a level of hydration that is less than a level of hydration when the coating (on the device) is inserted into the body. Upon insertion of the device in the body, the hydrogel becomes more hydrated and the hydrogel material loosens around the embedded microparticulates. At the target site, the elastic substrate with coating is expanded. Along with the increased hydration, expansion of the coating promotes release the microparticulates from the coating. Microparticulates are transferred to tissue of the subject, and bioactive agent can be released to provide a therapeutic effect. Therefore, in this aspect of the invention, the coating has the properties of elasticity, and porosity when in an expanded state.

The coating can be formed from polymeric material (one or more polymers) that allows immobilization of the microparticulates in a non-expanded state. The polymeric material can include one or more homopolymers, copolymers, combinations or blends thereof useful for forming the matrix. In one preferred aspect, the polymeric material is used to form a flexible hydrogel matrix as the coating.

In some modes of preparation, a coating composition is formed that includes one or more matrix-forming polymer and microparticulates. Generally, the coating material is chosen and used in a composition suitable for forming a matrix with intact microparticulates. For example, a polymer can be chosen which is soluble in a liquid that does not destroy the microparticulates. In one desired mode of practice, a hydrophilic polymer is used to prepare an aqueous composition that also includes the microparticulates. The microparticulates are generally water insoluble, meaning that they do not readily dissolve in water.

In other cases, microparticulates are not included in a coating composition having the one or more matrix-forming polymer. In such a coating process, the microparticulates are used in a subsequent coating step where they become associated with the coated polymeric matrix.

Generally, a coating composition includes an amount and type of polymeric material that provides suitable physical properties (such as elasticity and microparticulate retention). In some aspects the amount of polymeric material used to form the matrix in the composition is at a concentration in the range of about 5 mg/mL to about 50 mg/mL, about 10 mg/mL to about 40 mg/mL, or about 10 mg/mL to about 20 mg/mL. In exemplary modes of practice the polymeric material is present in the coating composition at about 15 mg/mL.

The polymeric material can also include pendent photoreactive or polymerizable groups that can be activated to form a crosslinked matrix of polymer. The amount of polymer in the composition can also be chosen based on the level of derivatization with these groups.

One class of hydrophilic polymers useful as polymeric materials for matrix formation is synthetic hydrophilic polymers. Synthetic hydrophilic polymers that are biostable (i.e., that show no appreciable degradation in vivo) can be prepared from any suitable monomer including acrylic monomers, vinyl monomers, ether monomers, or combinations of any one or more of these types of monomers. Acrylic monomers include, for example, methacrylate, methyl methacrylate, hydroxyethyl methacrylate, hydroxyethyl acrylate, methacrylic acid, acrylic acid, glycerol acrylate, glycerol methacrylate, acrylamide, methacrylamide, dimethylacrylamide (DMA), and derivatives and/or mixtures of any of these. Vinyl monomers include, for example, vinyl acetate, vinylpyrrolidone, vinyl alcohol, and derivatives of any of these. Ether monomers include, for example, ethylene oxide, propylene oxide, butylene oxide, and derivatives of any of these.

Examples of polymers that can be formed from these monomers include poly(acrylamide), poly(methacrylamide), poly(vinylpyrrolidone), poly(acrylic acid), poly(ethylene glycol), poly(vinyl alcohol), and poly(HEMA). Examples of hydrophilic copolymers include, for example, methyl vinyl ether/maleic anhydride copolymers and vinyl pyrrolidone/(meth)acrylamide copolymers. Mixtures of homopolymers and/or copolymers can be used.

Examples of some acrylamide-based polymers, such as poly(N,N-dimethylacrylamide-co-aminopropylmethacrylamide) and poly(acrylamide-co-N,N-dimethylaminopropylmethacrylamide) are described in example 2 of Applicants' co-pending U.S. Patent Pub. No. 2006/0030669 filed Sep. 17, 2004 (Taton et al.).

In some embodiments, the hydrophilic polymer is a vinyl pyrrolidone polymer, or a vinyl pyrrolidone/(meth)acrylamide copolymer such as poly(vinylpyrrolidone-co-methacrylamide). If a PVP copolymer is used, it can be a copolymer of vinylpyrrolidone and a monomer selected from the group of acrylamide monomers. Exemplary acrylamide monomers include (meth)acrylamide and (meth)acrylamide derivatives, such as alkyl(meth)acrylamide, as exemplified by dimethylacrylamide, and aminoalkyl(meth)acrylamide, as exemplified by aminopropylmethacrylamide and dimethylaminopropylmethacrylamide. For example, poly(vinylpyrrolidone-co-N,N-dimethylaminopropylmethacrylamide) is described in example 2 of U.S. Patent Pub. No. 2006/0030669 (Taton et al.).

In one embodiment, the polymers and copolymers as described are derivatized with one or more photoactivatable group(s). Exemplary photoreactive groups that can be pendent from biostable hydrophilic polymer include aryl ketones, such as acetophenone, benzophenone, anthraquinone, anthrone, quinone, and anthrone-like heterocycles. This provides a hydrophilic polymer having a pendent activatable photogroup that can be applied to the elastic substrate, and then treated with actinic radiation sufficient to activate the photogroups and cause covalent bonding to a target, such as the material of the elastic substrate. Use of photo-hydrophilic polymers can be used to provide a durable coating of a flexible hydrogel matrix, with the hydrophilic polymeric materials covalently bonded to the material of the elastic substrate.

A hydrophilic polymer having pendent photoreactive groups can be used to prepare the flexible hydrogel coating. Methods of preparing hydrophilic polymers having photoreactive groups are known in the art. For example, methods for the preparation of photo-PVP are described in U.S. Pat. No. 5,414,075. Methods for the preparation of photo-polyacrylamide are described in U.S. Pat. No. 6,007,833.

In another embodiment, the polymers and copolymers as described are derivatized with one or more polymerizable group(s). Polymers with pendent polymerizable groups are commonly referred to macromers. The polymerizable group(s) can be present at the terminal portions (ends) of the polymeric strand or can be present along the length of the polymer. In one embodiment polymerizable groups are located randomly along the length of the polymer. Polymerizable groups can be activated form a crosslinked matrix in which the microparticulates are immobilized.

Optionally, the coating can include a cross-linking agent. A crosslinking agent can promote the association of polymers in the coating, or the bonding of polymers to the coated surface. The choice of a particular crosslinking agent can depend on the ingredients of the coating composition.

Some exemplary crosslinking agents include two or more activatable groups, which can react with the polymers in the composition. Exemplary activatable groups include photoreactive groups as described herein, like aryl ketones, such as acetophenone, benzophenone, anthraquinone, anthrone, quinone, and anthrone-like heterocycles.

The photoactivatable cross-linking agent can be ionic, and can have good solubility in an aqueous composition. Thus, in some embodiments, at least one ionic photoactivatable cross-linking agent is used to form the coating. The ionic cross-linking agent can include an acidic group or salt thereof, such as selected from sulfonic acids, carboxylic acids, phosphonic acids, salts thereof, and the like. Exemplary counter ions include alkali, alkaline earths metals, ammonium, protonated amines, and the like.

Exemplary ionic photoactivatable cross-linking agents include 4,5-bis(4-benzoylphenylmethyleneoxy) benzene-1, 3-disulfonic acid or salt; 2,5-bis(4-benzoylphenylmethyleneoxy)benzene-1,4-disulfonic acid or salt; 2,5-bis(4-benzoylmethyleneoxy)benzene-1-sulfonic acid or salt; N,N-bis [2-(4-benzoylbenzyloxy)ethyl]-2-aminoethanesulfonic acid or salt, and the like. See U.S. Pat. No. 6,278,018.

In other aspects of the invention, biodegradable coating materials are used. Examples of biodegradable coating materials include those that can be used optionally as a control-release factor for the microparticulates.

For example, in aspect of the invention, the microparticulates are embedded in, and/or attached to, a fracturable, biodegradable coating that is present on the elastic substrate. In a non-expanded state, the microparticulates are substantially or entirely entrapped in the coating, or adhered to a coated layer, or both. Upon expansion of the substrate, the coating fractures and delaminates from the elastic surface. Therefore, the coating can have properties of rigidity and brittleness.

At the target site, portions of the coating are transferred to tissue along with the entrapped microparticulates. In some cases the portions of the transferred coating can adhere to the tissue and provide a barrier or skin to improve the immobilization of the microparticulates to the tissue.

Along with degradation of the biodegradable coating materials, bioactive agent can be released to provide a therapeutic effect.

The coating can be composed of biodegradable polymeric material (one or more polymers) that allows immobilization of the microparticulates. The polymeric material can include one or more homopolymers, copolymers, combinations or blends thereof useful for forming the matrix.

Natural polymers can also be used to form the matrix. Natural polymers include polysaccharides, for example, polydextrans, carboxymethylcellulose, and hydroxymethylcellulose; glycosaminoglycans, for example, hyaluronic acid; polypeptides, for example, soluble proteins such as collagen, albumin, and avidin; and combinations of these natural polymers. Combinations of natural and synthetic polymers can also be used.

Examples of natural biodegradable polymeric material suitable for the preparation of a biodegradable coating that can fracture and delaminate upon expansion of the elastic substrate are described in U.S. Patent Pub. Nos. 2005/ 0255142 and 2006/0165872 (supra). The biodegradable coating can be prepared by cross-linking low molecular weight biodegradable polysaccharides such as maltodextrin, amylose, and polyalditol, through use of pendent coupling groups. Generally, in order to form a coated layer, the polymeric material applied to the surface is treated to activate the coupling groups, thereby crosslinking the polymers to form a polymer matrix.

Other specific examples of biodegradable materials useful for the preparation of a biodegradable coating include polylactide, polygylcolide, polydioxanone, poly(lactide-co-glycolide), poly(glycolide-co-polydioxanone), polyanhydrides, poly(glycolide-co-trimethylene carbonate), and poly(glycolide-co-caprolactone). Generally, in order to form a coated layer, theses polymeric materials can be applied to the surface and dried.

Other examples of biodegradable materials useful for the preparation of a biodegradable coating include biodegradable poly(ester-amides) (e.g., as in U.S. Pat. No. 6,703,040), biodegradable polyetherester copolymers (e.g., PEG/PBT polymers as in U.S. Pat. No. 5,980,948), ester-containing block copolymers (e.g., as in U.S. Pat. No. 5,252,701 or EP 1555278), and degradable dextran-based polymers (e.g., as described in U.S. Pat. No. 6,303,148).

As an example, a biodegradable coating on an elastic substrate can be made by preparing a coating composition including a biodegradable multiblock copolymer, such containing glycolic acid, caprolactone, and PEG polymeric blocks, dissolved in acetone at 30 mg/mL and applied by spraying the solution onto the balloon (with or without a hydrogel base coat). Bioactive agent (e.g., in microparticulate form) can be dissolved into the coating solution (1-50% by weight), or can be applied after the degradable coating is formed. For example, paclitaxel (dissolved in methanol, or present as microparticulates in water) can be applied to the biodegradable coating.

The coating composition used to form the biodegradable coating can include one or more additional biocompatible polymers. For example, a secondary, tertiary, etc. biocompatible polymer can be included in the coating composition to form a coating with desired properties. The one or more additional polymers can increase the degradation of the coating. In some aspects, the biodegradable polymer is formed from a biodegradable polymer, such as polylactide, and a biocompatible polymer, such as one selected from the group consisting of poly(ethylene glycol) (PEG), poly(ethylene oxide), and poly(propylene oxide).

The amount of microparticulates associated with the surface of an elastic substrate can be chosen based on one or more factors, such as the amount of bioactive agent loaded into the microparticulates, the rate of release of bioactive agent, and the total amount of bioactive agent to be made available to a subject following release of the microparticulates. The total amount of microparticulates can include one set of microparticulates for delivery of one bioactive agent, or two or more sets of microparticulates for delivery of two or more bioactive agents.

The substrate can be coated with microparticulates in an amount sufficient to provide a desired therapeutic response when transferred to a subject and the bioactive agent of the microparticulates is made available. In some aspects, the surface of the elastic substrate can have a high density of microparticulates. In turn, this facilitates delivery of therapeutically effective amounts of bioactive agent over extended periods of time. Based on various factors, such as the density of the microparticulates in association with the elastic substrate, an amount of bioactive agent per unit area of the surface of the elastic substrate can be determined (e.g., μg bioactive agent per $cm^2$ surface). In some aspects, the amount of microparticulates associated with the substrate is in the range of about 0.05 $\mu g/mm^2$ to about 30 $\mu g/mm^2$, and in more specific embodiments in the range of about 1 $\mu g/mm^2$ to about 3 $\mu g/mm^2$.

Various methods can be performed to associate the polymeric material and the microparticulates with the surface of the elastic substrate. In many modes of practice, a coating composition including polymeric material and microparticulates is prepared and then applied to the surface of the elastic substrate. In one mode of practice a coating composition is used including microparticulates at a concentration in the range of about 10 mg/mL to about 50 mg/mL.

However, in some cases polymeric material can be applied to the surface independently of the microparticulates. For example, a polymeric composition can be applied to the surface in a first step, and then in a second step a composition having microparticulates (and without polymeric coating material) can be to the applied to the previously coated polymer. In one mode of practice a coating composition having microparticulates at a concentration in the range of about 10 mg/mL to about 50 mg/mL (without polymeric coating material) is used. Additional, optional, steps can be performed to apply the same or other polymeric material, such as a topcoat, over the microparticulates.

In one preferred aspect, a coating is formed on the surface of the elastic substrate using a spray coating process. In a particular mode of practice a balloon catheter is mounted on an apparatus that can manipulate the balloon for coating using a spray deposition process. An exemplary apparatus for coating a balloon catheter is shown in FIG. 9.

On the coating apparatus 91, the catheter portion 92 of the balloon catheter is secured within a track between a split cylindrical housing 93. The balloon portion 95 of the balloon catheter can be inflated using an inflator. The housing 94 is capable of rotation about the axis of the cylinder and is driven by a standard variable speed motor. The tip of the balloon 95 is retained within a circular grommet 96 but is free to rotate. To coat the surface of the balloon, the entire fixture can move underneath the spray coating flux produced by a spray head 97.

Further aspects and details of the balloon coating apparatus and method can be found in commonly owned provisional Application having Ser. No. 61/188,929, filed on Aug. 14, 2008, and entitled METHOD AND APPARATUS FOR COATING BALLOON CATHETERS (Chappa et al.).

Alternatively, a coating composition is dip-coated onto the surface of the elastic substrate to form a coated surface. In yet another method, the composition is brushed onto the surface of the elastic substrate.

Typically, the thickness of the coating on the elastic portion is greater than the diameter of the largest microparticulate being disposed during the coating process. In some applications, the substrate can be subject to more than one step of coating with a mixture of polymeric material and microparticulates, thereby allowing the formation of multiple layers on the substrate surface.

In some aspects, a coating is prepared by treating the coating materials that are disposed on the elastic substrate. For example, the coating composition can include a reactive group, that when activated, causes crosslinking of polymeric material and formation of the coating. The polymeric material used to form the coating can include pendent polymerizable groups, such as acrylate groups. The free radical polymerization of the polymerizable groups can be caused by the activation of a photoactivatable reagent that is a polymerization initiator. The applied composition can be treated with UV light to activate the polymerization initiator.

Microparticulates can be associated with the coating to provide partially embedded particles using a variety of techniques. In one technique a flexible hydrogel layer is formed on the surface of the expandable elastic substrate. Next an aqueous composition containing microparticulates is disposed on the surface of the flexible hydrogel layer. The water in the aqueous composition causes at least the surface of the flexible hydrogel layer to swell. The swelling makes the flexible hydrogel layer at least partially permeable to the microparticulates deposited on the hydrogel layer, and microparticulates move into the polymeric material of hydrogel layer. After a sufficient amount of time allowing for the microparticulates to move partially into the hydrogel layer, water can then be removed, such as by evaporation, heating, or vacuum. Removal of water causes the hydrogel layer to shrink from a swollen state, physically constrain the microparticulates, and results in the partial embedding of a substantial portion of the microparticulates deposited on the surface of the hydrogel layer.

If the surface of the flexible hydrogel matrix coating is visualized, a significant proportion of the microparticulates will be seen as (a) fully embedded in the hydrogel matrix just under the surface, and partially embedded in the hydrogel matrix (a portion in and a portion that is out), and partially embedded where the microparticulates are "stuck" to the hydrogel surface.

In many cases, the microparticulates that are deposited and partially entrapped in the hydrogel layer are non-soluble in an aqueous composition. For example, the microparticulates are composed of a non-soluble bioactive agent.

The microparticulates can be associated with an elastic surface present on an insertable medical article. The "insertable" medical article can be one that is introduced into a mammal for the prophylaxis or treatment of a medical condition. The "insertable" medical article can be used for short term use, or longer term treatment. An "implantable" medical article can more specifically refer to those insertable medical intended for longer term insertion (i.e., placement) at a target site in the body, such a period of days, weeks, or months.

These devices include any that are introduced subcutaneously, percutaneously or surgically to rest within an organ, tissue, or lumen of an organ, such as arteries, veins, ventricles, or atria of the heart.

Exemplary medical articles include vascular implants and grafts, grafts, surgical devices; synthetic prostheses; vascular prosthesis including endoprosthesis, stent-graft, and endovascular-stent combinations; small diameter grafts, abdominal aortic aneurysm grafts; hemostatic barriers; mesh and hernia plugs; ASD, PFO, and VSD closures; percutaneous closure devices, mitral valve repair devices; left atrial appendage filters; valve annuloplasty devices, catheters; central venous access catheters, vascular access catheters, abscess drainage catheters, drug infusion catheters, parenteral feeding catheters, intravenous catheters (e.g., treated with antithrombotic agents), stroke therapy catheters, blood pressure and stent graft catheters; anastomosis devices and anastomotic closures; aneurysm exclusion devices; infection control devices; membranes; tissue scaffolds; tissue-related materials; shunts including cerebral spinal fluid (CSF) shunts, glaucoma drain shunts; dental devices and dental implants; ear devices such as ear drainage tubes, tympanostomy vent tubes; ophthalmic devices; spinal and neurological devices; nerve regeneration conduits; neurological catheters; neuropatches; orthopedic devices such as orthopedic joint implants, bone repair/augmentation devices, cartilage repair devices; urological devices and urethral devices such as urological implants, bladder devices, renal devices and hemodialysis devices, colostomy bag attachment devices; biliary drainage products.

The insertable medical device can also have one or more non-elastic portions. For example, in a balloon catheter, the catheter portion can be the non-elastic portion. The non-elastic portion can be partially or entirely fabricated from a plastic polymer. Plastic polymers include those formed of synthetic polymers, including oligomers, homopolymers, and copolymers resulting from either addition or condensation polymerizations. Examples of suitable addition polymers include, but are not limited to, acrylics such as those polymerized from methyl acrylate, methyl methacrylate, hydroxyethyl methacrylate, hydroxyethyl acrylate, acrylic acid, methacrylic acid, glyceryl acrylate, glyceryl methacrylate, methacrylamide, and acrylamide; vinyls such as ethylene, propylene, vinyl chloride, vinyl acetate, vinyl pyrrolidone, vinylidene difluoride, and styrene. Examples of condensation polymers include, but are not limited to, nylons such as polycaprolactam, polylauryl lactam, polyhexamethylene adipamide, and polyhexamethylene dodecanediamide, and also polyurethanes, polycarbonates, polyamides, polysulfones, poly(ethylene terephthalate), polydimethylsiloxanes, and polyetherketone.

The non-elastic portion can also be partially or entirely fabricated from a metal. Metals that can be used in medical articles include platinum, gold, or tungsten, as well as other metals such as rhenium, palladium, rhodium, ruthenium, titanium, nickel, and alloys of these metals, such as stainless steel, titanium/nickel, nitinol alloys, cobalt chrome alloys, non-ferrous alloys, and platinum/iridium alloys. One exemplary alloy is MP35.

In an exemplary embodiment, the insertable medical device comprises a balloon catheter. Balloon catheter constructions are well known in the art and are described in various documents, for example, U.S. Pat. Nos. 4,195,637, 5,041,089, 5,087,246, 5,318,587, 5,382,234, 5,571,089, 5,776,101, 5,807,331, 5,882,336, 6,394,995, 6,517,515, 6,623,504, 6,896,842, and 7,163,523. Balloon catheters generally include four portions, the balloon, catheter shaft, guidewire, and manifold. A balloon catheter generally includes an elongated catheter shaft with the inflatable balloon attached to a distal section of the catheter shaft. At a proximal end of the catheter shaft, there is typically a manifold. At the manifold end, placement of the catheter can be facilitated using a guidewire. Guidewires are small and maneuverable when inserted into an artery. Once the guidewire is moved to the target location, the catheter with balloon portion is then fed over the guidewire until the balloon reaches the target location in the vessel. The balloon is then inflated when the catheter reaches the targeted constriction to thereby apply the requisite mechanical force to cause vessel dilation. The manifold can also control the fluid introduction within shaft for expansion of the balloon. The balloon is typically inserted into the arterial lumen of a patient and advanced through the lumen in an unexpanded state.

Figure 10A:
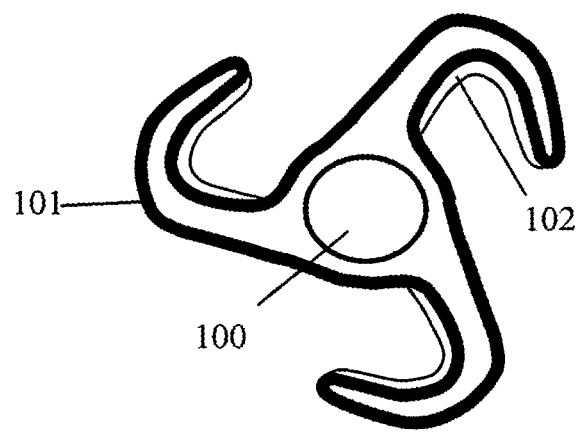
FIGS. 10a and 10b are cross sectional views of a balloon having a coating on portions of the balloon.
Figure 10B:
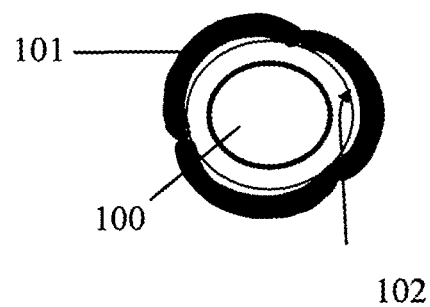

Prior to inflation the balloon can be folded to a compacted configuration for delivery to the target site. A folding process may involve creating "arms" of the balloon material and folding these arms inward (towards the catheter axis) to compact the balloon material. Using such a folding pattern, there will be portions of the balloon material (when the balloon is folded and compacted) that face the outside, and portions of the balloon material that face the inside, the inner-facing portions representing "protected" surfaces. Accordingly, and in another coating embodiment, the inner-facing surfaces of the balloon material include a coating of polymeric material associated with microparticulates. FIG. 10a shows a cross sectional view of a deflated balloon, with a central catheter portion 100, and the balloon material in the shape of arms 101 with one side of the arm 102 having a polymeric coating associated with microparticulates. FIG. 10b shows a cross sectional view of a deflated balloon folded into a compacted configuration, with a central catheter portion 100, and the side of the arm 102 having a polymeric coating associated with microparticulates folded inwards on the central catheter portion 100. The balloon surface can be coated using a spray coating apparatus, as described herein, to provide a pattern wherein the balloon in a compacted folded configuration has protected (inner) coated surfaces associated with microparticulates.

The balloon is typically inflated using a fluid, which is injected through an inflation port. The mechanics of fluid transfer and introduction within balloons vary according to the specific design of the catheter, and are well known in the art.

A balloon catheter with the inventive microparticulate-associated surface of the invention can be used in a balloon angioplasty procedure. Balloon angioplasty is commonly carried out for the treatment of diseased arteries to reduce atherosclerotic stenosis or to recanalize occluded arteries. In such a procedure, obstructed intraluminal passages are reopened or dilated by inflation of the balloon at the occluded site. According to the invention, balloon catheter having a microparticulate associated balloon portion is inserted percutaneously into a luminal passage of a patient, such as an artery, vein, or airway. Once inserted, the balloon is advanced to the desired treatment site, where the balloon is inflated to dilate the luminal passage. According to the invention, bioactive agent loss as the balloon is advanced is minimized or eliminated.

Upon inflation of the balloon, a portion of the microparticulates that are associated with the surface of the balloon are transferred to the tissue of lumenal arterial wall at the target site. In some aspects, the portion transferred can be about 10% or greater of the amount of microparticulates originally associated with the surface, about 20% or greater, about 30% or greater, about 40% or greater, about 50% or greater, about 60% or greater, about 70% or greater, about 80% or greater, or about 90% or greater. In some aspects the amount of microparticulates transferred is in the range of about 30% to 100%.

For example, in aspects wherein the microparticulates are included in an expandable coating on the surface of the balloon, the inflation of the balloon stretches the coating. The coating on the surface of the balloon can undergo physical changes that promote the release of the microparticulates. Upon insertion in a subject, the flexible hydrogel matrix can become more hydrated, resulting in a loosening of the matrix material around the microparticulates. Also, the stretching of the coating (upon balloon expansion) can cause it to effectively become thinner than the coating on the balloon in an unexpanded state. In addition, the stretching of the coating can create pores in the coating from which the microparticulates can escape. The hydration, thinning of the coating and/or the creation of the pores can effectively cause the microparticulates to "pop out" of the coating upon balloon expansion.

The microparticulates that are transferred can adhere to the arterial tissue at the target site. Accordingly, the microparticulates can release bioactive agent at the target site, which can have a therapeutic effect on the tissue. The release of the drug at the target site can be useful to control tissue response after balloon dilation. For example, the microparticulates can release an antiproliferative agent, such as sirolimus or paclitaxel that can inhibit neointimal proliferation at the dilated site. As another example, the microparticulates can release an antithrombotic agent, such as heparin, that can inhibit clotting.

In some aspects, microparticulates can be used to release bioactive agent at the target site in a sustained profile. This feature allows for release of the bioactive agent from the microparticulates over a longer and more therapeutically useful time period. In some aspects, the microparticulates include a bioactive agent and a biodegradable polymer that modulates the release of the bioactive agent over a period of days to a few months.

Example 1

The elastic surface of the balloon of a balloon catheter was provided with a flexible hydrogel coating with associated paclitaxel microparticulates. The balloon catheter that was used in the coating process was obtained from Minnesota Medtec (Maple Grove, Minn.). The elastic portion of the balloon was made from nylon and has a balloon wall thickness of 5-10 µm.

A hydrogel coating solution was prepared using photo-polyacrylamide (prepared as described U.S. Pat. No. 6,007,833, Examples 1 & 2), which was weighed and dissolved into a mixture of IPA and water (50% IPA/50% water (v/v)) at a concentration of 10 mg/mL. The balloon was coated in the photo-polyacrylamide coating solution using a dip process with a withdrawal rate of 0.5 cm/s. After the hydrogel coating solution was applied to the balloon, it was subjected to UV cure. The coated balloon was placed in front of a Dymax 2000-EC Series UV Floodlamb with a 400 Watt metal halide bulb, approximately 20 cm from light source, illuminated for three minutes, and then removed.

Next, paclitaxel microparticulates were prepared using a wet milling process. Briefly, neat drug was added directly to DI water at 20 mg/mL. The precipitated paclitaxel particulates were then milled in water to reduce the particle size to ~1-3 µm The drug/water suspension was tumble milled in a glass jar with ceramic beads. The suspension was milled for 16 hours (overnight) at approximately 100 rpm. The resulting suspension was then applied to the photo-polymer coated surface by pipetting a known volume of drug suspension (typically 20 µl). The pipetted droplet was evenly distributed over the balloon surface by rotating the balloon until the solvent was visibly dry.

Figure 11A:
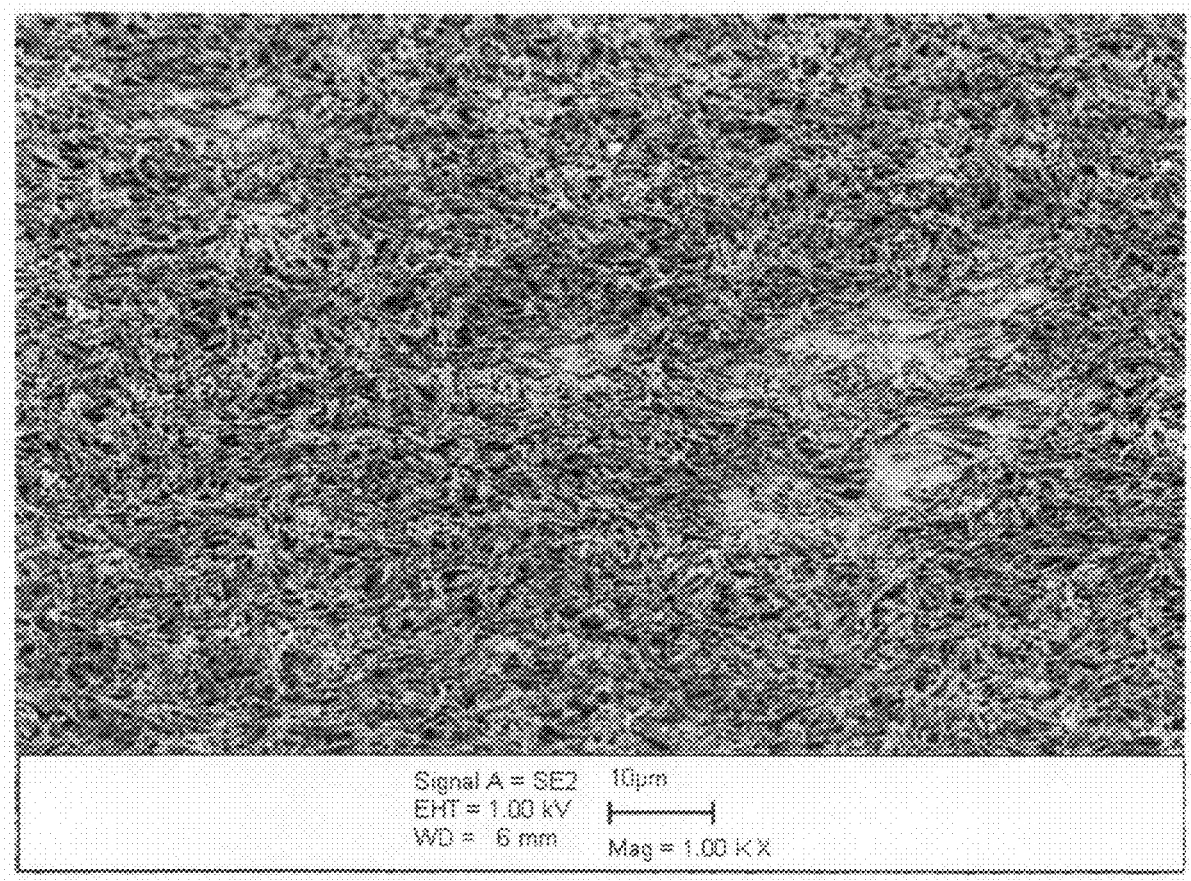
FIGS. 11a and 11b are micrographs of a balloon substrate having a hydrogel coating with paclitaxel microparticulates partially embedded in the hydrogel.
Figure 11B:
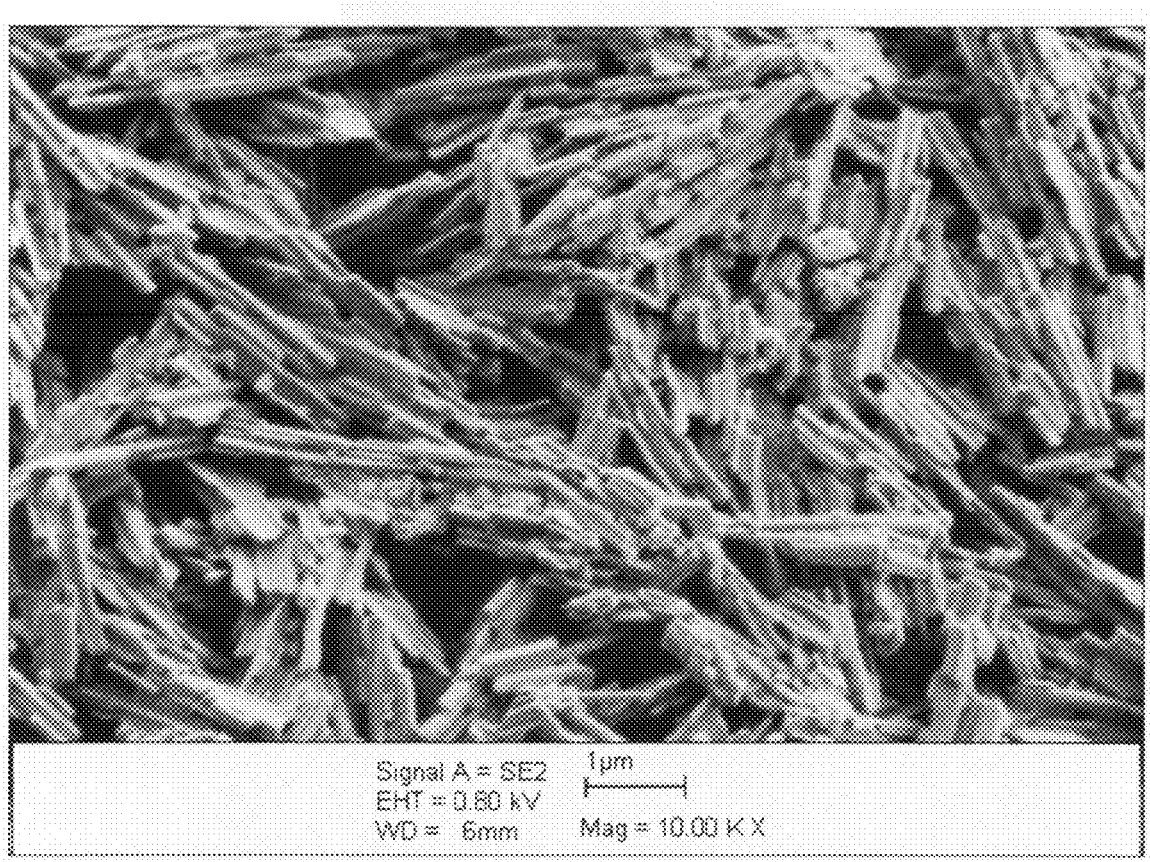

FIGS. 11a and 11b are micrographs of the elastic substrate having a hydrogel coating with paclitaxel microparticulates partially embedded in the hydrogel, prepared according to this method.

Example 2

The coating process as described in Example 1 was repeated, with the exception of the use of a different coating composition to form the hydrogel coated layer.

A hydrogel coating solution was prepared using photo-polyacrylamide (Example 1) at 5 mg/mL, photo-poly(vinylpyrrolidone) (prepared as described in Example 4 of U.S. Pat. No. 5,414,075) at 25 mg/mL, poly(vinylpyrrolidone) K90 (BASF) at 10 mg/mL, and 4,5-bis(4-benzoylphenylmethyleneoxy) benzene-1,3-disulfonic acid (prepared as described in U.S. Pat. No. 6,278,018 (Example 1)) at 0.25 mg/mL, dissolved into a mixture of IPA and water (15% IPA/85% water).

Dipcoating, UV treatment, and paclitaxel microparticulate coating was performed as described in Example 1.

Example 3

The elastic surface of the balloon of a balloon catheter was provided with a flexible hydrogel coating and then paclitaxel microparticulates were formed on the hydrogel surface.

The coating processes as described in Examples 1 and 2 were repeated to provide hydrogel coated layers.

Next, a microparticulate-forming composition was prepared by dissolving paclitaxel in methanol at a concentration of 30 mg/mL. The composition was then applied to the photo-polymer coated surfaces by pipetting a known volume of drug suspension (typically 10-20 µl). The pipetted droplet was evenly distributed over the balloon surface by rotating the balloon until the solvent was visibly dry.

Figure 12A:
FIGS. 12a and 12b are micrographs of a balloon substrate having a hydrogel coating with paclitaxel microparticulates partially embedded in the hydrogel.
Figure 12B:
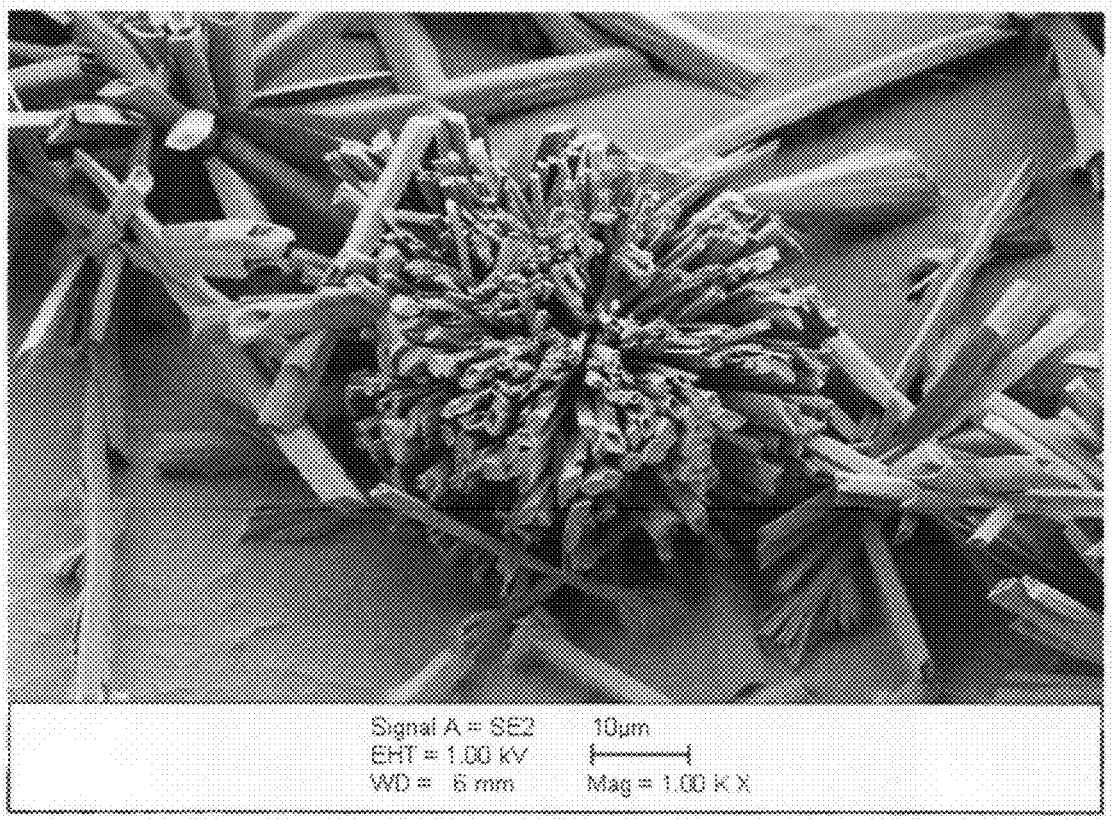

FIGS. 12a and 12b are micrographs of the elastic substrate having a hydrogel coating with paclitaxel microparticulates partially embedded in the hydrogel, prepared according to this method.

Example 4

Microparticulate transfers from paclitaxel microparticulate-coated balloons having hydrogel coatings were tested in a silicone tube model.

Silicone tubing (inner diameter: 0.125 inch; outer diameter: 0.188 inch; wall: 0.0315 inch; Cole-Parmer Instrument Co.) was obtained and cut into 1.5 inch lengths. The silicone tubing pieces were then placed individually in 4 mL amber glass vial filled with 4 mL of PBS (phosphate buffer saline) pH-7.4, which was preheated in a water bath to 37° C.

A deflated, folded balloon (prepared according to Example 1) was placed in a 8 mL vial (filled with 8 mL of PBS (phosphate buffer saline) pH-7.4, which was preheated in a water bath to 37° C.) and soaked for 4 min. The balloon was then slid into the inner lumen of the silicone tube (submerged inside 4 mL vial) and then expanded for 30 sec at 4 atm. Pressure was then released and the balloon was removed from the tubing.

To determine the amount of paclitaxel transferred to the wall of the inner lumen of the tubing, the tubing was submerged in 4 mL of a mixture of 0.1% glacial acetic acid in methanol for 24 hours. A 350 µL aliquot of the extraction media was then transferred to 96 well plate for drug content measurement by UV (@ 232 nm).

The amounts of paclitaxel transferred to the silicone tubing are shown in Table 1.

TABLE 1

| Coating | Paclitaxel transferred to silicone tube (% of Total Load) |
| --- | --- |
| As prepared in Example #1 | 26.5% |
| As prepared in Example #2 | 35.6% |
| As prepared in Example #3 | 3.5% |

Example 5

Microparticulate transfers from paclitaxel microparticulate-coated balloons having hydrogel coatings were tested in an ex-vivo C model.

Harvested porcine artery was obtained and cut into 1.5 inch lengths. The porcine artery pieces were then placed in a 4 mL amber glass vial filled with 4 mL of PBS (phosphate buffer saline) pH-7.4, which was preheated in a water bath to 37° C.

A deflated, folded balloon (prepared according to Example 1) was placed in the 8 mL vial (filled with 8 mL of PBS (phosphate buffer saline) pH-7.4, which was preheated in a water bath to 37° C.) and soaked for 4 min. The balloon was then slid into the inner lumen of the porcine artery (submerged inside 4 mL vial) and then expanded for 30 sec at 4 atm. Pressure was then released and the balloon was removed from the porcine artery.

To determine the amount of paclitaxel transferred to the wall of the inner lumen of the porcine artery, the porcine artery was submerged in 4 mL of a mixture of 0.1% glacial acetic acid in methanol for 24 hours. A 1 mL aliquot of the extraction media was then transferred to 96 well plate for drug content measurement by UV.

The amounts of paclitaxel transferred to the porcine artery are shown in Table 2.

TABLE 2

| Coating | Paclitaxel transferred to porcine artery (% of Total Load) |
| --- | --- |
| As prepared in Example #1 | N/A -- Not Tested |
| As prepared in Example #2 | 36.6% |

What is claimed is:

1. An insertable medical device to deliver a water-insoluble bioactive agent to an inner lumen of a blood vessel of a subject, the device comprising:
    (a) an expandable elastic portion of an angioplasty balloon,
    (b) a flexible biostable hydrogel matrix layer comprising a biodegradable multiblock copolymer and an alkyl methacrylate, wherein the flexible biostable hydrogel matrix forms a coating on an outer surface of the expandable elastic portion of the angioplasty balloon, and
    (c) a water-insoluble bioactive agent that is both in neat form and in the form of microparticulates having an average greatest dimension in the range of 0.1-10 microns and associated with a surface of the flexible biostable hydrogel matrix;
    wherein the water-insoluble bioactive agent that is both in neat form and in the form of microparticulates contacts and is released to the inner lumen of the blood vessel upon expansion of the expandable elastic portion of the angioplasty balloon in the blood vessel.

2. The device of claim 1, wherein flexible biostable hydrogel matrix further comprises a polymer having pendent reacted photogroups that covalently bond the polymer to a target selected from other polymers in the flexible biostable hydrogel matrix and the outer surface of the expandable elastic portion.

3. The device of claim 2, wherein the pendent reacted photogroups comprise a reacted aryl ketone photogroup.

4. The device of claim 1, wherein the balloon is a folded angioplasty balloon.

5. The device of claim 1, wherein the water-insoluble bioactive agent is selected from the group consisting of antiproliferative, antiinflammatory, and antiplatelet compounds.

6. The device of claim 1, wherein the water-insoluble bioactive agent is a water-insoluble antiproliferative agent.

7. The device of claim 1, wherein the flexible biostable hydrogel matrix has a thickness in the range of 5-100 microns.

8. The device of claim 1, wherein the microparticulates are on surface of the flexible biostable hydrogel matrix and are formed by a process including a step of drying a suspension of the microparticulates in water on a surface of the flexible biostable hydrogel matrix.

9. The device of claim 1, wherein the microparticulates have an average greatest dimension in the range of 1-3 microns.

10. The device of claim 1, wherein the flexible biostable hydrogel matrix is non-contiguous.

11. An insertable medical device comprising a coated expandable elastic angioplasty balloon portion capable of delivering a water-insoluble bioactive agent to an inner lumen of a blood vessel of a subject, the coating comprising
    (i) a flexible biostable hydrogel matrix comprising a biodegradable multiblock copolymer and an alkyl methacrylate coated on an outer surface of the expandable elastic angioplasty balloon portion, wherein the flexible bio stable hydrogel matrix forms a coating on the outer surface of the expandable elastic angioplasty balloon portion; and
    (ii) water-insoluble bioactive agent that is both in neat form and in the form of microparticulates which is associated with the flexible biostable hydrogel matrix and which disassociates from the expandable elastic angioplasty balloon portion during expansion of the expandable elastic angioplasty balloon portion to release the water-insoluble bioactive agent.

12. A method for delivering a water-insoluble antiproliferative agent to a blood vessel of a subject comprising the steps of:
    1) providing an insertable medical device comprising:
        (a) an expandable elastic portion of an angioplasty balloon,
        (b) a flexible biostable hydrogel matrix layer comprising a biodegradable multiblock copolymer and an alkyl methacrylate, wherein the flexible biostable hydrogel matrix forms a coating on an outer surface of the expandable elastic portion of the angioplasty balloon, and (c) a water-insoluble antiproliferative agent that is both in neat form and in the form of microparticulates having an average greatest dimension in the range of 0.1-10 microns, and which is associated with a surface of the flexible biostable hydrogel matrix;

2) inserting the medical device into the blood vessel of the subject; and 3) expanding the expandable elastic portion in the blood vessel, wherein the water-insoluble antiproliferative agent that is both in neat form and in the form of microparticulates disassociates from the insertable medical device and is released into the inner lumen of the blood vessel to provide a therapeutic effect to tissue of the subject.

13. The device of claim 1 wherein the biodegradable multiblock copolymer comprises one or more functional groups selected from the group consisting of amides, carbonates, esters, urethanes, and combinations thereof.

* * * * *